(12) United States Patent
Que et al.

(10) Patent No.: US 7,875,038 B2
(45) Date of Patent: Jan. 25, 2011

(54) RELEASABLE BASKET AND METHOD OF MAKING THEREOF

(75) Inventors: Like Que, Union City, CA (US); James A. Teague, Spencer, IN (US); James S. Bates, Sparta, NJ (US); Stéphane Gobron, Mt. Prospect, IL (US); Tim Ward, Bedford, IN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1050 days.

(21) Appl. No.: 11/652,078

(22) Filed: Jan. 11, 2007

(65) Prior Publication Data

US 2007/0135820 A1 Jun. 14, 2007

Related U.S. Application Data

(63) Continuation of application No. 09/979,166, filed as application No. PCT/US00/14315 on May 24, 2000, now Pat. No. 7,169,154.

(60) Provisional application No. 60/135,876, filed on May 25, 1999.

(51) Int. Cl.
*A61B 17/22* (2006.01)
(52) U.S. Cl. .................................... 606/127
(58) Field of Classification Search ................ 606/113, 606/114, 127, 159, 200
See application file for complete search history.

(56) References Cited

U.S. PATENT DOCUMENTS

| | | | |
|---|---|---|---|
| 651,395 A | 6/1900 | Strapp |
| 2,556,783 A | 6/1951 | Wallace |
| 2,767,703 A | 10/1956 | Nieburgs |
| 3,137,298 A | 6/1964 | Glassman |
| 3,472,230 A | 10/1969 | Fogarty |
| 3,828,790 A | 8/1974 | Curtiss et al. |
| 3,955,578 A | 5/1976 | Chamness et al. |
| 3,996,938 A | 12/1976 | Clark, III |
| 4,046,150 A | 9/1977 | Schwartz et al. |
| 4,198,960 A | 4/1980 | Utsugi |
| 4,243,040 A | 1/1981 | Beecher |
| 4,299,225 A | 11/1981 | Glassman |

(Continued)

FOREIGN PATENT DOCUMENTS

AU 56865/86 4/1986

(Continued)

OTHER PUBLICATIONS

Vorwerk, Dierk et al., "Percutaneous Embolectomy: In Vitro Investigations of the Self-expanding Tulip Sheath", Radiology (1992) 182: 415-418.

(Continued)

*Primary Examiner*—Kevin T Truong
(74) *Attorney, Agent, or Firm*—Finnegan, Henderson, Farabow, Garrett & Dunner, LLP

(57) ABSTRACT

A medical retrieval device includes a basket formed of two or more loops. The basket may be used to retrieve material (e.g., a urinary stone) from a body. The basket opens and closes for end-encapsulation of a stone and is strengthened by support members that interconnect the basket loops. A captured stone may be from the basket with the basket still in the body by opening the loops.

11 Claims, 26 Drawing Sheets

U.S. PATENT DOCUMENTS

| | | |
|---|---|---|
| 4,326,530 A | 4/1982 | Fleury, Jr. |
| 4,347,846 A | 9/1982 | Dormia |
| 4,425,908 A | 1/1984 | Simon |
| 4,447,227 A | 5/1984 | Kotsanis |
| 4,557,255 A | 12/1985 | Goodman |
| 4,590,938 A | 5/1986 | Segura et al. |
| 4,611,594 A | 9/1986 | Grayhack et al. |
| 4,612,931 A | 9/1986 | Dormia |
| 4,625,726 A | 12/1986 | Duthoy |
| 4,650,466 A | 3/1987 | Luther |
| 4,655,219 A | 4/1987 | Petruzzi |
| 4,682,599 A | 7/1987 | Konomura |
| 4,691,705 A | 9/1987 | Okada |
| 4,699,147 A | 10/1987 | Chilson et al. |
| 4,706,671 A | 11/1987 | Weinrib |
| 4,718,419 A | 1/1988 | Okada |
| 4,723,549 A | 2/1988 | Wholey et al. |
| 4,728,319 A | 3/1988 | Masch |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,873,978 A | 10/1989 | Ginsburg |
| 4,885,003 A | 12/1989 | Hillstead |
| 4,893,621 A | 1/1990 | Heyman |
| 4,907,572 A | 3/1990 | Borodulin et al. |
| 4,926,858 A | 5/1990 | Gifford, III et al. |
| 4,927,426 A | 5/1990 | Dretler |
| 4,927,427 A | 5/1990 | Kriauciunas et al. |
| 4,994,079 A | 2/1991 | Genese et al. |
| 4,998,539 A | 3/1991 | Delsanti |
| 5,011,488 A | 4/1991 | Ginsburg |
| 5,030,201 A | 7/1991 | Palestrant |
| 5,041,093 A | 8/1991 | Chu |
| 5,053,008 A | 10/1991 | Bajaj |
| 5,057,114 A | 10/1991 | Wittich et al. |
| 5,064,428 A | 11/1991 | Cope et al. |
| 5,071,407 A | 12/1991 | Termin et al. |
| 5,084,054 A | 1/1992 | Bencini et al. |
| 5,098,440 A | 3/1992 | Hillstead |
| 5,100,423 A | 3/1992 | Fearnot |
| 5,102,415 A | 4/1992 | Guenther et al. |
| 5,133,733 A * | 7/1992 | Rasmussen et al. ......... 606/200 |
| 5,171,233 A | 12/1992 | Amplatz et al. |
| 5,176,688 A | 1/1993 | Narayan et al. |
| 5,192,286 A | 3/1993 | Phan et al. |
| 5,290,294 A | 3/1994 | Cox et al. |
| 5,311,858 A | 5/1994 | Adair |
| 5,329,942 A | 7/1994 | Gunther et al. |
| 5,330,482 A | 7/1994 | Gibbs et al. |
| 5,345,936 A | 9/1994 | Pomeranz et al. |
| 5,354,310 A | 10/1994 | Garnic et al. |
| 5,376,100 A | 12/1994 | Lefebvre |
| 5,421,832 A | 6/1995 | Lefebvre |
| 5,486,183 A | 1/1996 | Middleman et al. |
| 5,496,330 A | 3/1996 | Bates et al. |
| 5,499,981 A | 3/1996 | Kordis |
| 5,549,626 A | 8/1996 | Miller et al. |
| 5,562,678 A | 10/1996 | Booker |
| 5,658,296 A | 8/1997 | Bates et al. |
| 5,693,069 A | 12/1997 | Shallman |
| 5,891,153 A | 4/1999 | Peterson |
| 5,906,622 A | 5/1999 | Lippitt et al. |
| 6,159,220 A | 12/2000 | Gobron et al. |
| 6,348,056 B1 * | 2/2002 | Bates et al. ................. 606/114 |

FOREIGN PATENT DOCUMENTS

| | | |
|---|---|---|
| DE | 2821048 | 11/1979 |
| DE | 3213223 A1 | 10/1983 |
| DE | 3407708 A1 | 9/1985 |
| DE | 3501707 A1 | 7/1986 |
| DE | 8707515 U1 | 9/1987 |
| DE | 8707516 U1 | 10/1987 |
| DE | 3620385 C1 | 1/1988 |
| DE | 3633527 A1 | 4/1988 |
| DE | 4025799 A1 | 2/1992 |
| DE | 32 13 223 A1 | 10/1993 |
| EP | 0160870 A2 | 11/1985 |
| EP | 0 195 444 | 9/1986 |
| EP | 0 428 998 A1 | 5/1991 |
| EP | 0 737 450 A1 | 10/1996 |
| FR | 2 694 687 | 2/1994 |
| FR | 2694687 A1 | 2/1994 |
| GB | 2 020 557 A | 11/1979 |
| WO | WO 91/11209 | 8/1991 |
| WO | WO 92/05828 | 4/1992 |
| WO | WO 94/24946 | 11/1994 |
| WO | WO 95/05129 | 2/1995 |
| WO | WO 96/01591 | 1/1996 |
| WO | WO 99/16363 | 4/1999 |

OTHER PUBLICATIONS

Vorwerk, Dierk et al., "Percutaneous Balloon Embolectomy with a Self-expanding Tulip Sheath: In Vitro Experiments", Radiology (1995) 197: 153-156.

International Search Report published with International Application No. PCT/US2000/14315, (May 2000).

International Preliminary Examination Report from International Application No. PCT/US2000/14315, (May 2000).

Written Opinion from International Application No. PCT/US2000/14315, (May 2000).

* cited by examiner

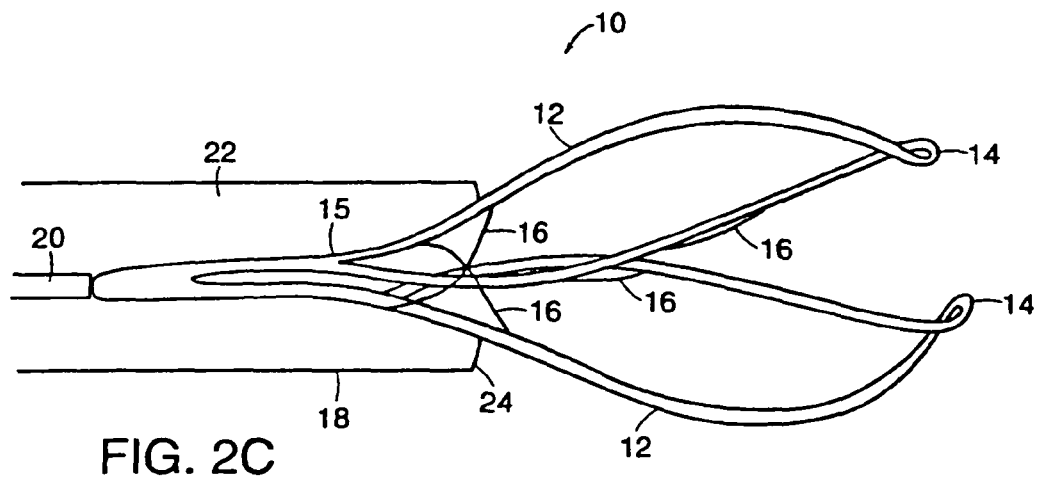
FIG. 2C
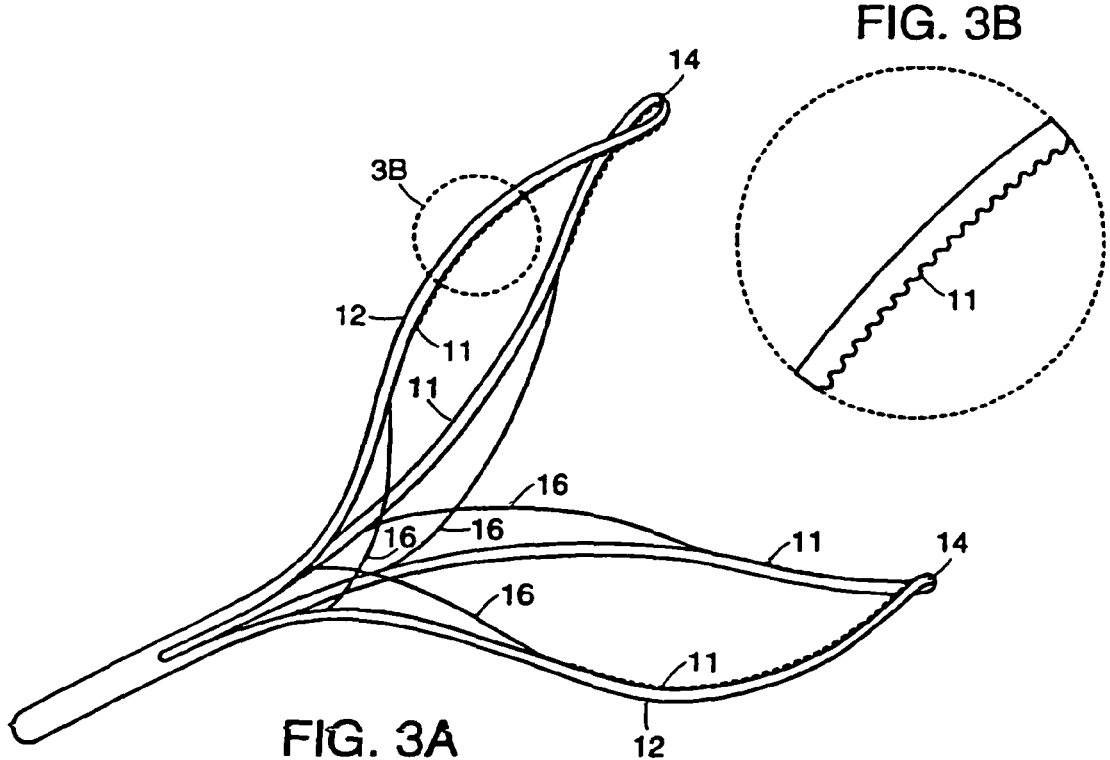
FIG. 3B
FIG. 3A

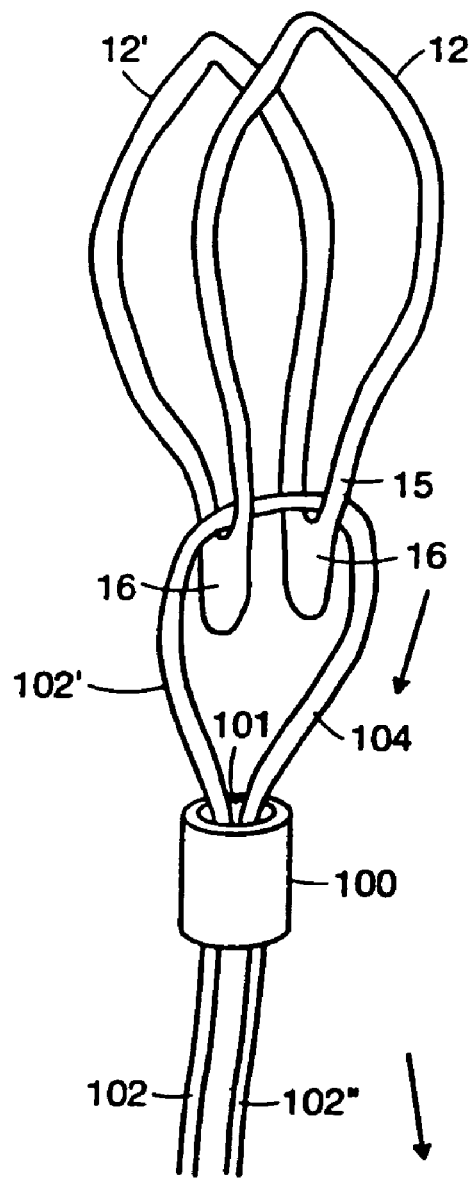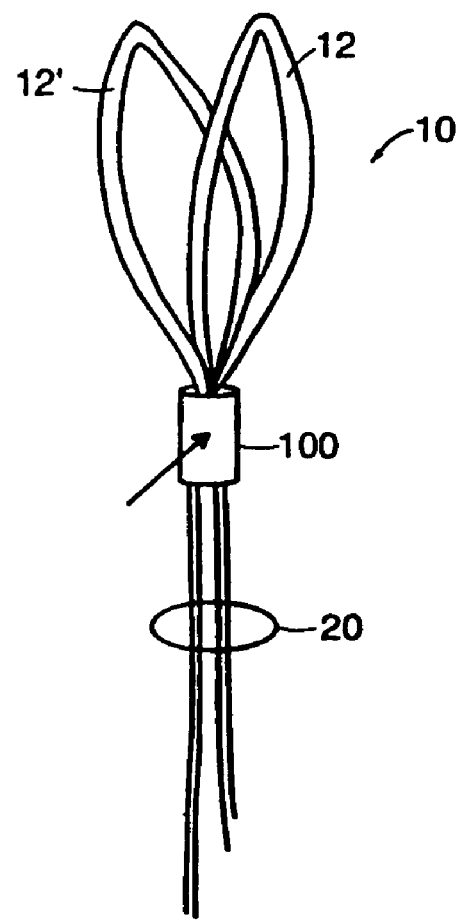
FIG. 9F
FIG. 9G

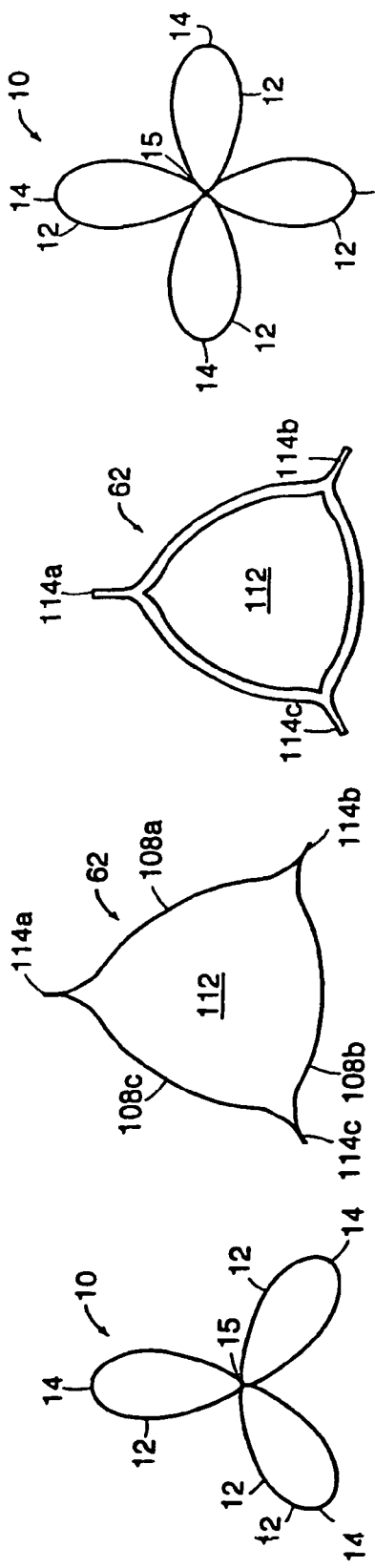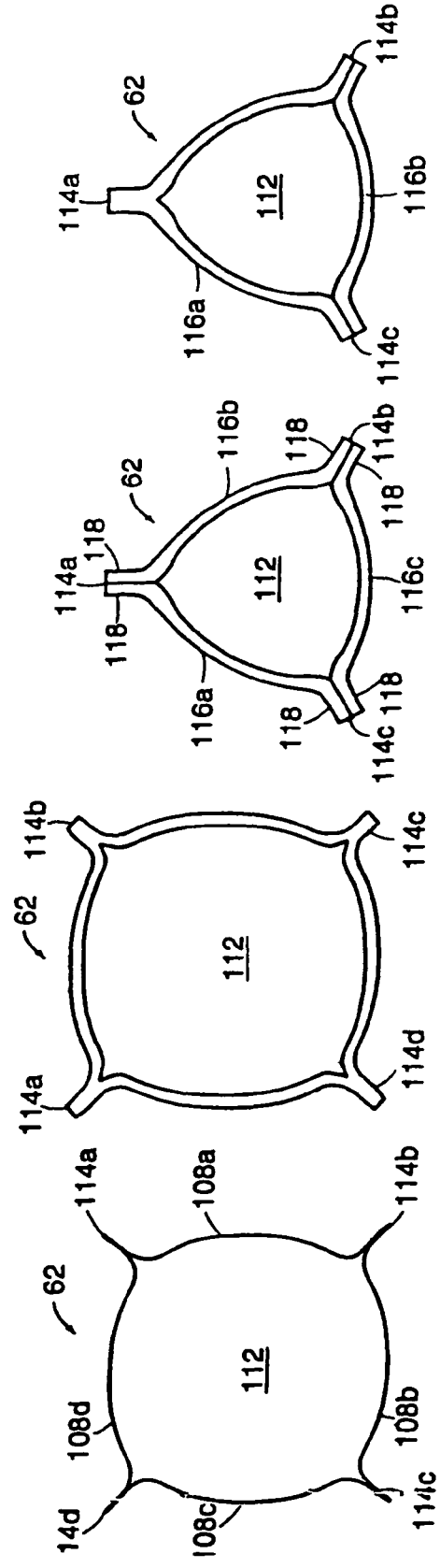

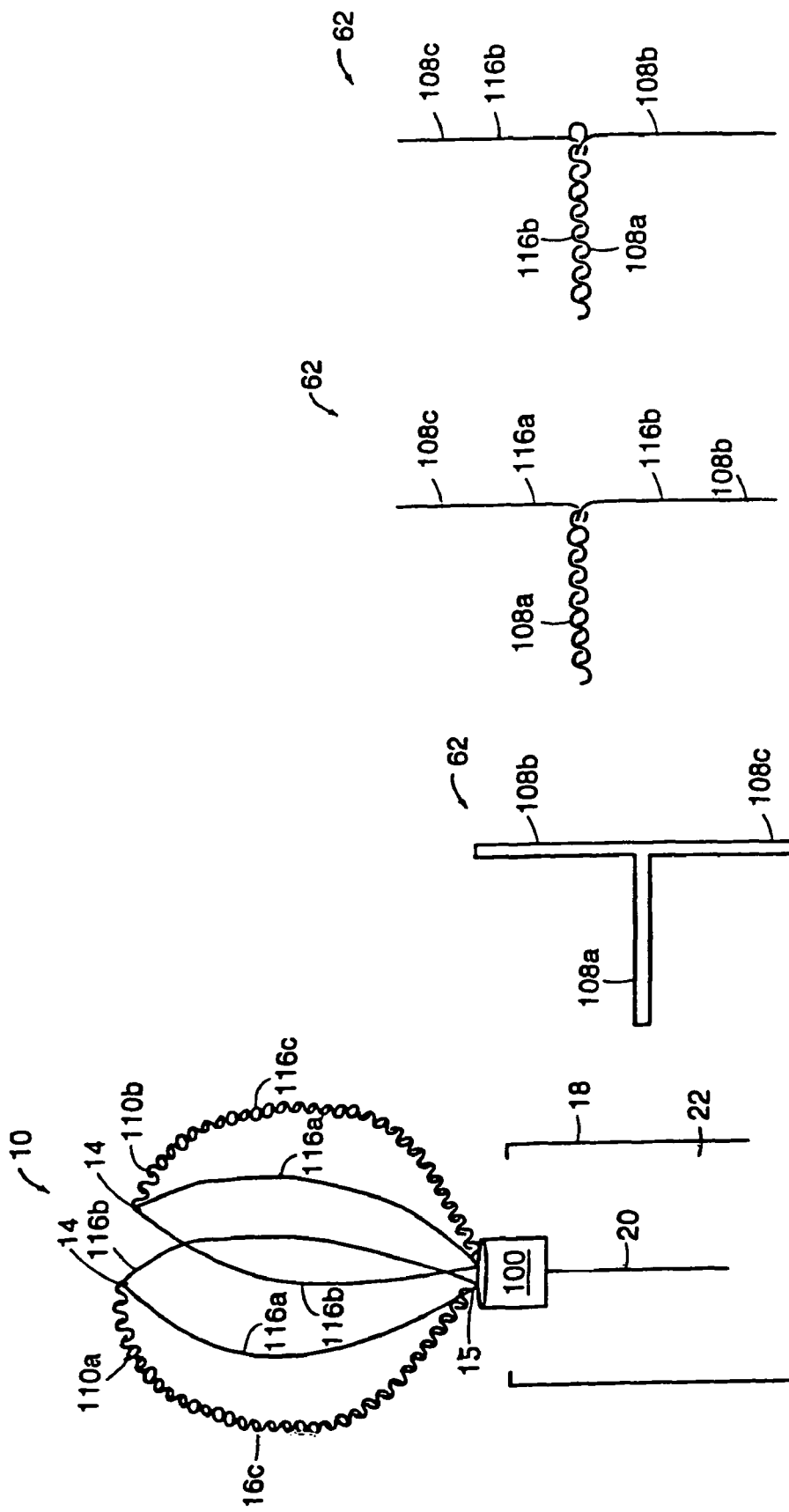

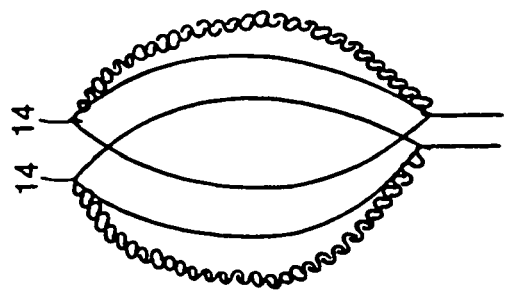
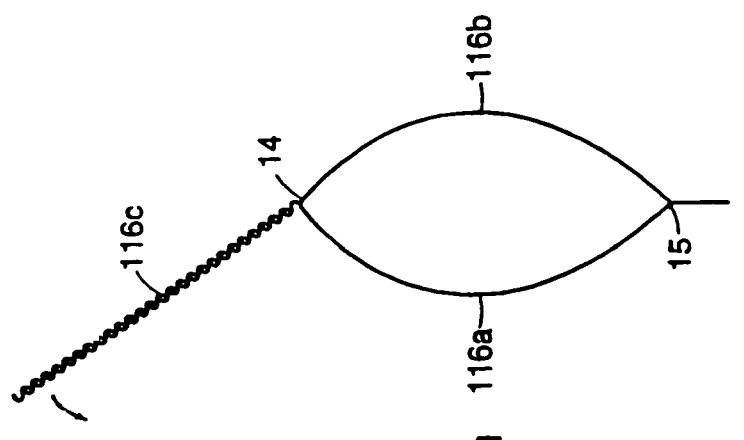
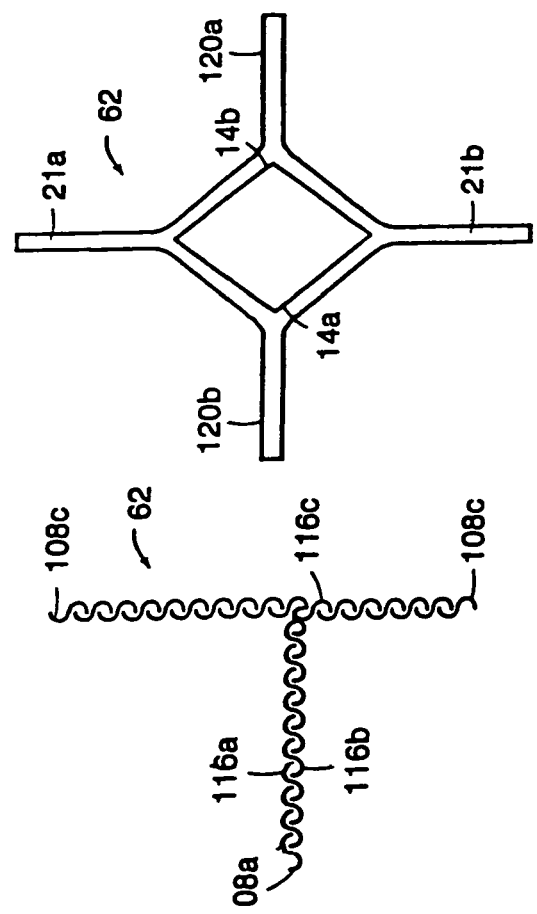
FIG. 12H
FIG. 12G
FIG. 12F
FIG. 12E

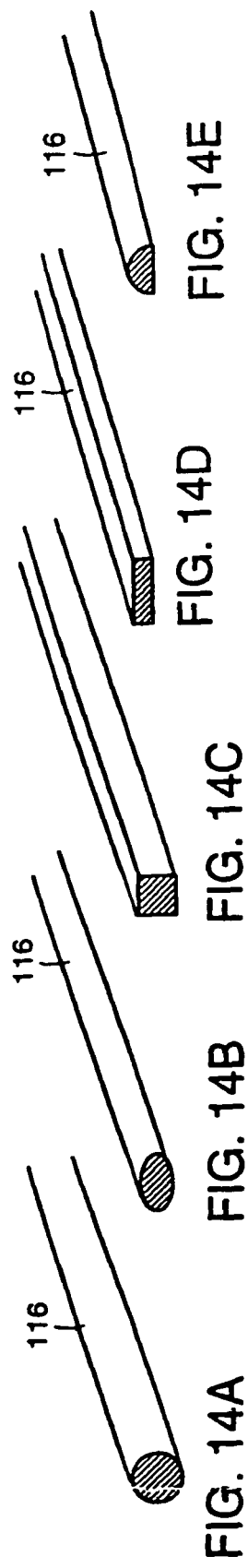
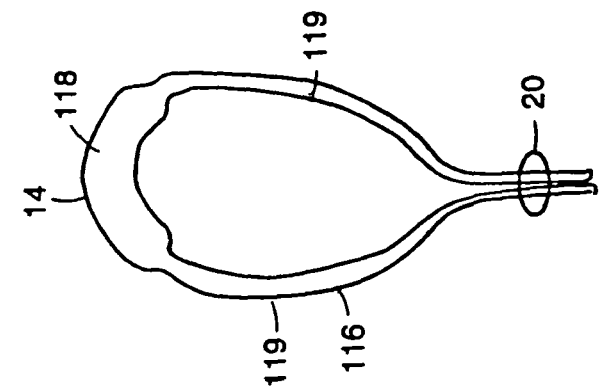
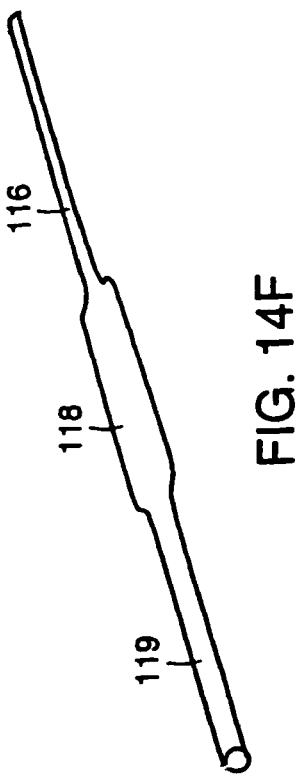
FIG. 14A
FIG. 14B
FIG. 14C
FIG. 14D
FIG. 14E
FIG. 14F
FIG. 14G

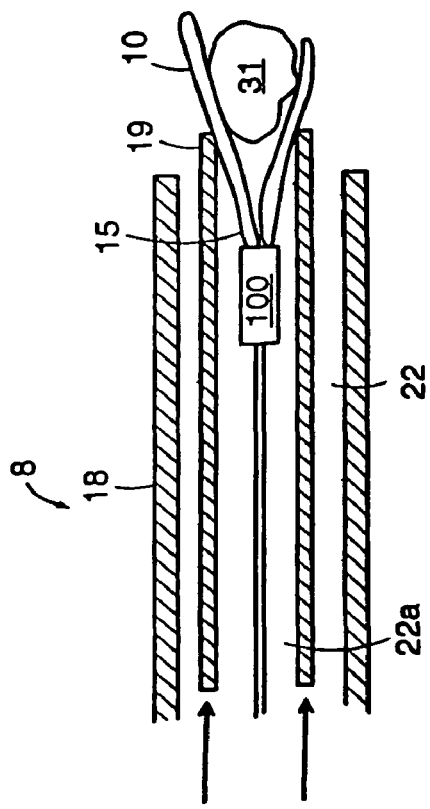
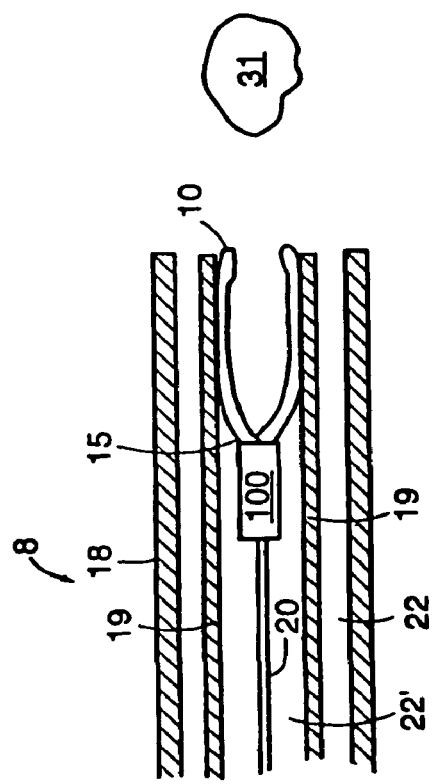
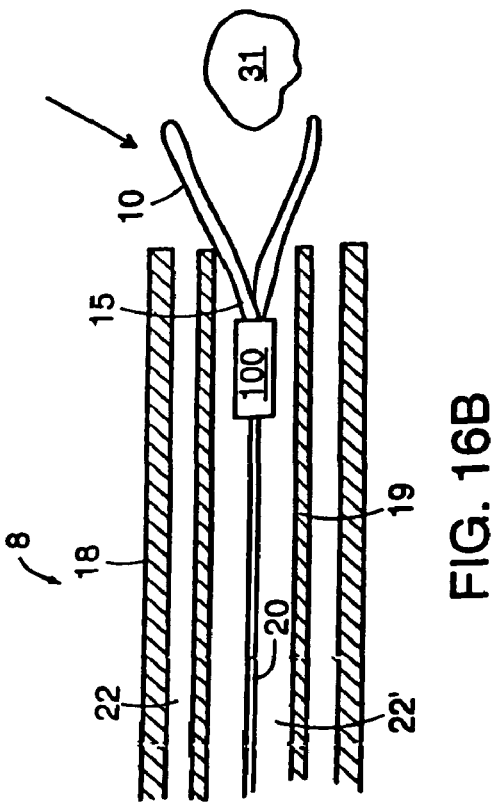
FIG. 16C
FIG. 16A
FIG. 16B

RELEASABLE BASKET AND METHOD OF MAKING THEREOF

CROSS-REFERENCE TO RELATED APPLICATION

The application is a continuation of U.S. application Ser. No. 09/979,166, filed on Apr. 15, 2002now U.S. Pat. No. 7,169,154, which is the national phase of International (PCT) Patent Application Ser. No. PCT/US2000/14315, filed May 24, 2000, published under PCT Article 21(2) in English, which is based on provisional U.S. patent application Ser. No. 60/135,876, filed on May 25, 1999. The entire contents of these applications are incorporated herein by reference.

TECHNICAL FIELD

The invention generally relates to medical devices such as retrieval assemblies for retrieving material from within a body and methods of making retrieval assemblies. More particularly, the invention relates to retrieval assemblies such as baskets for retrieval of stones such as urinary tract stones, gall stones, and other biological materials.

BACKGROUND INFORMATION

Medical retrieval assemblies such as baskets generally are used to retrieve biological and foreign material from the body including stones. Such baskets may be used through an endoscope or a laparoscope, for example.

In existing medical retrieval baskets, the contour of the baskets generally are round, oval, or pear-shaped, and the baskets are formed by a plurality of legs. Stones or other biological materials are captured in the basket by moving the basket around the material to be retrieved and maneuvering the material into the basket through the space between the basket legs.

After the material is captured in a known basket, it is generally difficult to release the material from the basket if release of the captured material is required or indicated. The technical difficulty in releasing material such as a captured stone is a characteristic of known medical retrieval baskets in general. In some patients with long-standing clinical problems with urinary tract stones, a cicatrix may form in the tract as a result of trauma to its lining. The stenosis created by the cicatrix may not be so narrow so as to interfere with insertion of a retrieval basket while the basket is in a closed position. However, after the basket is expanded to capture the stone that is lodged beyond the stenotic area of the tract, the diameter of the basket containing the captured stone may exceed the diameter of the stenotic region of the urinary tract. Under these circumstances, release of the stone from the basket is a prerequisite for withdrawal of the device from the urinary tract. If the stone can not be released, more invasive, surgical approaches are required to disengage the stone from the basket.

Also, known baskets must be eased beyond the stone or to one side of the stone to permit entry of the stone into the basket. This maneuver can be technically very difficult. The narrow diameter of the tract lumen, compounded by the formation of stretch resistant scar tissue in the tract at the sites of the stone can severely limit the space around which the basket can maneuver. Moreover, the tract lining may become so attenuated at the site of the stone that advancing the basket to one side of the stone may risk rupture of the tract.

When expanded, existing baskets also generally lack dilatative strength. That is, known baskets generally are not resistive to forces countering basket expansion. The lack of dilatative strength in existing baskets is usually the result of flexible basket legs which are helpful in facilitating the entry of a stone into the basket but which decrease dilatative strength. Consequently, existing baskets generally are not effective at dilating the tract.

SUMMARY OF THE INVENTION

In one aspect, the invention relates to medical retrieval baskets with enhanced basket strength and with features that permit both end-encapsulation and, when indicated, release of biological material. The basic medical retrieval basket design as contemplated by the invention is an end-encapsulation basket formed by a plurality of loops. Baskets according to the invention have several advantages over other known baskets. One advantage is the feature that allows stone capture by end-encapsulation. The basket is formed by a plurality of loops, the loops are joined at the basket base, and have an unattached end at the distal portion of the basket. The basket loops are moveable between a closed position and an open position. In the open position, the ends of the loops are parted. When the basket is maneuvered into a body tract to capture material such as a stone, the basket is in a withdrawn position collapsed within the sheath. As the end of the sheath approaches the stone, the basket is extended from the sheath. The basket loops are moved between a closed position and an open position where the unattached ends of the loops are parted. With the unattached ends of the loops parted, the basket is advanced directly over the stone at the front end of the basket. The stone is end-encapsulated when the stone enters the basket through the space created by the parted unattached ends of the basket loops. The end-encapsulation basket design obviates the need for passing the basket to one side of or beyond the stone in order to capture the stone. The basket can "pluck" stones from embedded regions such as the calyx of a kidney. Once the stone is captured in the basket, the unattached ends of the basket loops are juxtaposed by returning the basket loops to the closed position. The stone is thereby captured and the medical retrieval device with the captured stone is removed from the body tract.

In one embodiment of the invention, the medical retrieval device comprises a proximal handle, an outer sheath extending distally from the handle and including a lumen extending therethrough from a distal end of the outer sheath to a proximal end of the outer sheath. An inner sheath includes a lumen extending therethrough from a distal end of the inner sheath to a proximal end of the inner sheath. The inner sheath is axially moveable in the lumen of the outer sheath relative to the outer sheath.

In this embodiment of the invention, at least two opposing loops have a collapsed position in which the loops are collapsed within the lumen of the inner sheath and another position in which the loops are extended from the distal end of the inner sheath and out of the lumen. The loops are joined at a base and unattached to each other at their distal ends. The loops are moveable between an open position and a closed position with the loops being closer together at their distal ends when in the closed position than when in the open position to allow captures and release of material.

In another embodiment of the invention, the medical retrieval device comprises a proximal handle and a sheath extending distally from the handle and having a lumen extending therethrough from a distal end of the sheath to a proximal end of the sheath. Opposing first and second hemi-baskets structures each comprise a loop and a back stay. The first and second hemi-baskets have a collapsed position in which the hemi-baskets are collapsed within the lumen of the sheath and another position in which the first and second hemi-baskets extend from the distal end of the inner sheath and out of the lumen. The hemi-baskets are joined at a base and unattached to each other at their distal ends. The hemi-baskets are moveable between an open position and a closed position with the first and second hemi-baskets being closer together at their distal ends when in the closed position than when in the open position to allow capture and release of material.

In yet another embodiment of the invention, the medical retrieval device comprises a proximal handle, and a sheath extending distally from the handle and including a lumen extending therethrough from a distal end of the sheath to a proximal end of the sheath. At least two opposing loops include a collapsed position in which the loops are collapsed within the lumen of the sheath and another position in which the loops are extended from the distal end of the sheath and out of the lumen. The loops are joined at a base and are unattached to each other at their distal ends. The loops are moveable between an open position and a closed position with the loops being closer together at their distal ends when in the closed position than when in the open position to allow capture and release of material. The device also comprises a base cannula and an elongated member including a first portion, a second portion, and an intermediate portion. The intermediate portion of the elongated member is inserted between the two loops and the first and second portion of the elongated member is inserted through the base cannula for securing the elongated member to the at least two loops.

At least a portion of at least the inner surfaces of the basket loops can be modified to improve stone gripping. For example, all or a portion of the inner surfaces of the loops can be coated with an anti-slip substance such as a rubberized material or roughened in some manner (e.g., by serrations, abrasions, etching, etc.) to increase friction between the inner surfaces of the basket loops and the captured material.

In another aspect of the invention, a method for manufacturing a medical retrieval basket comprises removing a flat frame from a single piece of construction material. The frame is symmetrical and has a first end and a second end, with the first and second ends being oppositely disposed. The frame is then folded such that the first and second ends of the frame are brought together, and the joined ends are then secured together.

In another embodiment of this aspect of the invention, the method for forming a retrieval assembly comprises forming a frame substantially in a plane. The frame comprises at least three loop members and at least three joining members connecting the loop members to define an aperture in the frame. The frame is folded to superimpose the joining members on one another to cause the loop members to form loops extending away from the joining members. The superimposed joining members are secured together.

In another embodiment of this aspect of the invention, the method for manufacturing a retrieval assembly comprises forming a first configuration comprising a substantially T-shape including three members, each member comprising a free end. One member is positioned perpendicular to the other two members. The two members of the first configuration are folded to form a first loop with an apex. The perpendicular member at the apex of the first loop is folded to form a first-hemi-basket including a back stay.

A second configuration is formed comprising a substantially T-configuration including three members, each member comprising a free end. One member is positioned perpendicular to the other two members. The two members of the second configuration are folded to form a second loop with an apex. The perpendicular member at the apex of the second loop is folded to form a second hemi-basket including a back stay.

The loop of the first hemi-basket is opposed to the loop of the second hemi-basket. The free ends of the three members of the first hemi-basket are secured to the free ends of the three members of the second hemi-basket to form the retrieval assembly.

In yet another embodiment for manufacturing a retrieval assembly according to the invention, a first loop is formed from a first length of wire including two ends. A second loop is formed from a second length of wire including two ends. The ends of the first length of wire are secured to the ends of the second length of wire to form a retrieval assembly comprising two loops.

Another method for manufacturing a retrieval device according to the invention features the steps of, forming a shape comprising at least two loops, and inserting a wire comprising a first end and a second end between the two loops. The first and second ends of the wire are pulled through a lumen of a cannula. The first and second ends of the wire are secured to a cable joined in a handle and the handle is positioned at the proximal end of the device.

BRIEF DESCRIPTION OF THE DRAWINGS

In the drawings, like reference characters generally refer to the same parts throughout the different views. Also the drawings are not necessarily to scale, emphasis generally being placed upon illustrating the principles of the invention.

FIG. 2C is a plan view of the device with the basket in an intermediate position between closed and open (FIG. 2B).

FIG. 3A is a plan view of basket loops according to the invention illustrating a modification of the inner surface of the basket loops.

FIG. 3B is an expanded view of a section of a basket loop shown in FIG. 3A.

FIGS. 9F-9G illustrate an embodiment of a method according to the invention for joining a basket to an elongated member.

FIG. 10A illustrates an end view of an embodiment of a three loop basket according to the invention.

FIG. 10B illustrates an embodiment of a shape according to the invention for forming the basket illustrated in FIG. 10A.

FIG. 10C illustrates an embodiment of a shape according to the invention for forming the basket illustrated in FIG. 10A.

FIG. 10D illustrates an end view of an embodiment of a four loop basket according to the invention.

FIG. 10E illustrates an embodiment of a shape according to the invention for forming the basket illustrated in FIG. 10D.

FIG. 10F illustrates an embodiment of a shape according to the invention for forming the basket illustrated in FIG. 10D.

FIG. 10G illustrates an embodiment of a shape according to the invention for forming the basket illustrated in FIG. 10A.

FIG. 10H illustrates an embodiment of a shape according to the invention for forming the basket illustrated in FIG. 10A.

FIG. 12A illustrates an embodiment of a basket including opposing hemi-baskets according to the invention.

FIG. 12B illustrates an embodiment of a shape for forming a portion of the basket illustrated in FIG. 12A.

FIG. 12C illustrates another embodiment of a shape for forming a portion of the basket illustrated in FIG. 12A.

FIG. 12D illustrates another embodiment of a shape for forming a portion of the basket illustrated in FIG. 12A.

FIG. 12E illustrates another embodiment of a shape for forming a portion of the basket illustrated in FIG. 12A.

FIG. 12F illustrates another embodiment of a shape for forming a portion of the basket illustrated in FIG. 12A.

FIG. 12G illustrates an intermediate step in the formation of a portion of the basket illustrated in FIG. 12A.

FIG. 12H illustrates an intermediate step in the formation of the basket illustrated in FIG. 12A.

FIGS. 14A-14F illustrate various embodiments of cross-sections of wires used to form the basket according to the invention.

FIG. 14G illustrates an embodiment of a basket loop formed from the wire illustrated in FIG. 14F.

FIG. 16A illustrates an embodiment of a retrieval device with two sheaths according to the invention.

FIG. 16B illustrates the retrieval device illustrated in FIG. 16A with the basket extended and open.

FIG. 16C illustrates the retrieval device illustrated in FIG. 16C with a stone captured in a partially closed basket.

DESCRIPTION

Figure 1A:
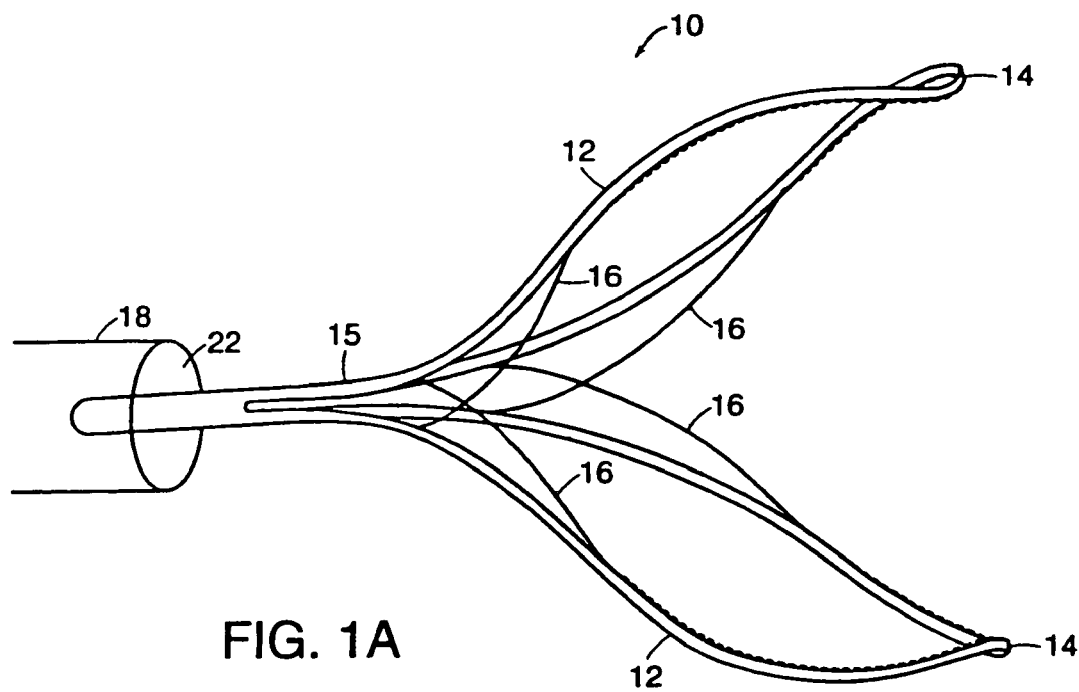
FIG. 1A is a plan view of a medical retrieval device according to the invention with the basket in the open position.
Figure 1B:
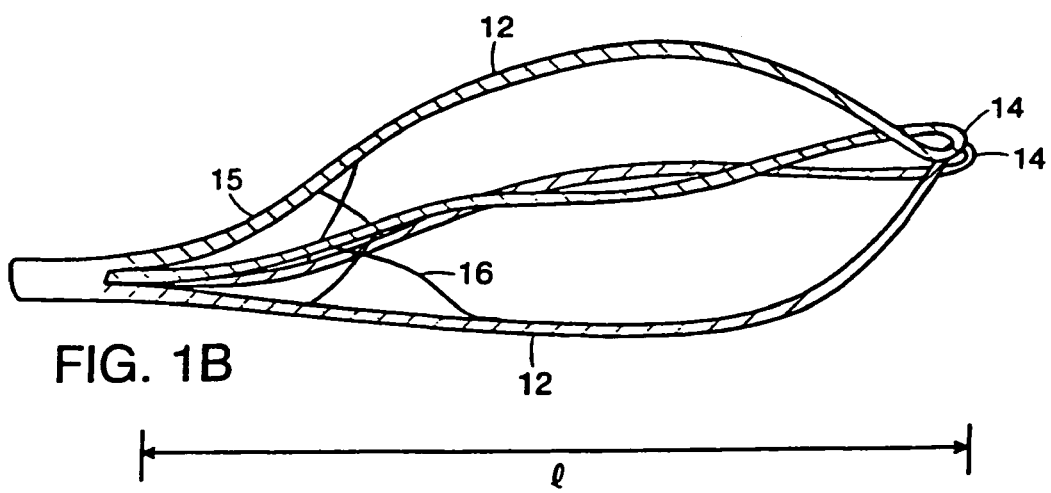
FIG. 1B is a plan view of the medical retrieval device of FIG. 1A with the basket in the closed position.
Figure 1C:
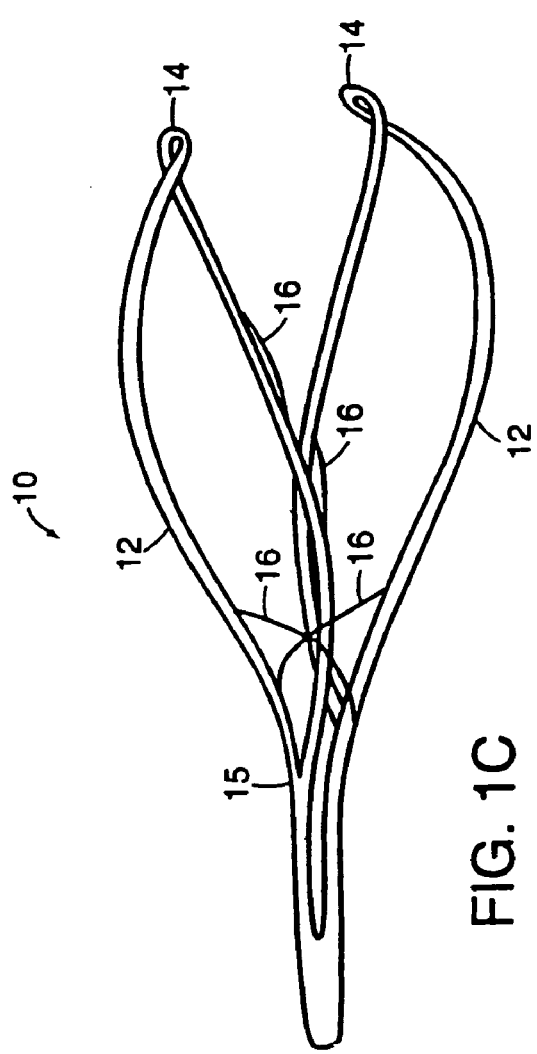
FIG. 1C is a plan view of a medical retrieval device with the basket in an intermediate position between closed (FIG. 1B) and open (FIG. 1A).
Figure 1D:
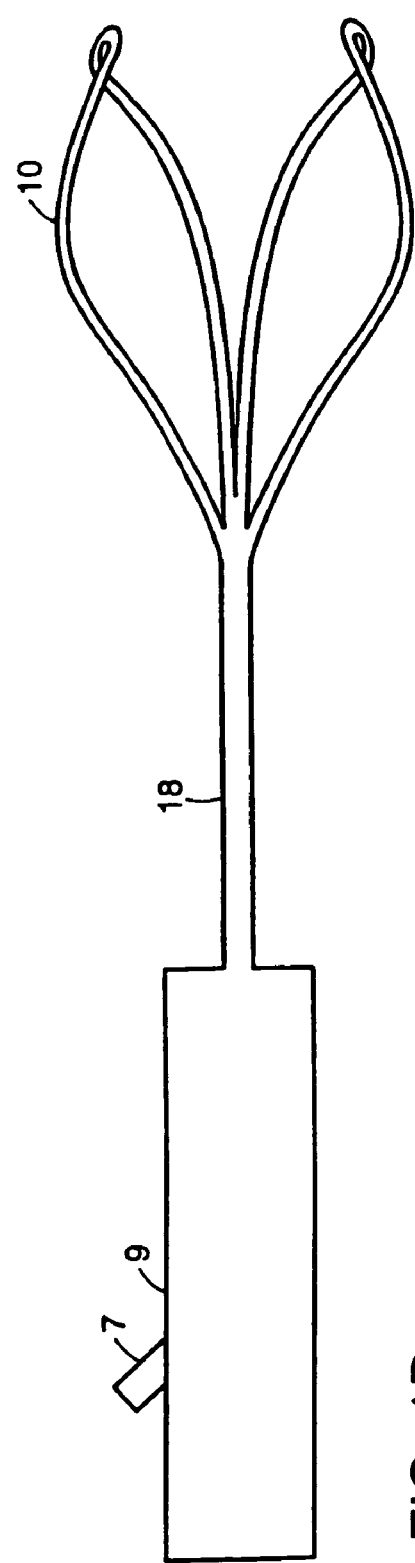
FIG. 1D shows a medical retrieval device according to the invention including a distal basket, an intermediate sheath, and a proximal handle.

Referring to FIGS. 1A and 1D, a retrieval device according to the invention includes a retrieval assembly 10, such as a basket, a catheter or sheath 18 for introduction of the basket 10 into a tract, and at least one elongated member such as a cable 20 extending and moveable within the sheath 18. As shown in FIG. 1D, the device also includes a proximal handle 9 at the proximal end of the sheath 18, and this handle typically includes one or more actuating mechanisms 7 (e.g., a slide, a knob, a dial, etc.) coupled to the sheath 18 and/or the cable 20 for causing the sheath 18 and the basket 10, under operator control, to move relative to each other to move the basket from a collapsed position within the sheath to an extended position outside of the sheath. The cable 20 generally can be any elongate member such as a cable, wire, coil, or shaft, for example. The basket 10 includes at least two basket loops 12. Each of the basket loops 12 has an unattached end 14 and a fixed end 15 at the basket base.

The basket 10 is moveable between an open position and a closed position. In FIG. 1A, the basket 10 is in an open position. When the basket 10 is in the open position, the unattached ends 14 of the basket loops 12 are parted as shown in FIG. 1A. When the basket 10 is in the closed position, as shown in FIG. 1B, the unattached ends 14 of the loops 12 are juxtaposed in that they are located close together. The basket 10 may assume any position between the open and closed positions. For example, the unattached ends 14 of the basket loops 12 may be parted to any intermediate position along an arc drawn by the unattached ends 14 of the basket loops 12 as the loops move between the closed position illustrated in FIG. 1B and the open position illustrated in FIG. 1A. FIG. 1C illustrates an exemplary intermediate position of the unattached ends 14 of the basket loops 12 between the open position of the basket 10 and the closed position of basket 10.

The basket loops 12 may be any shape, for example, generally oval (as shown in FIG. 1A), round, oblong, or asymmetrical. The basket loops 12 may be disposed in one or more planes as shown in FIG. 1A. Also, while two loops 12 are shown and described herein, it is possible to construct a device with two or more loops 12 and such devices are within the scope of the invention. For example, a device with three or four or more loops 12 is possible.

Also, the length of each of the loops 12 (1 in FIG. 1B) can be the same, or one can be slightly longer than the other such that the ends 14 do not exactly align upon closure. Having one loop longer than the other has been shown to help in collapsing the basket to its smallest profile such that it fits into a sheath 18 (FIG. 2A) easier.

Referring still to FIG. 1A, in a disclosed embodiment, the basket loops 12 are strengthened by support members 16. The support members 16 are struts disposed between the two opposing basket loops 12. The support members 16 or struts help to prevent scissoring of the basket loops in a horizontal plane and add strength to the basket in a vertical plane when the basket is expanded. It is possible to achieve a functioning basket without the members 16.

Figure 2A:
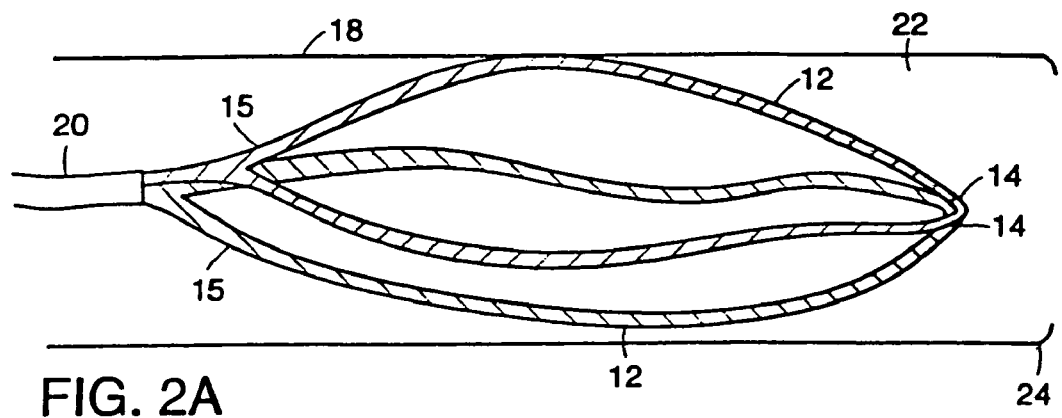
FIG. 2A is a plan view of a medical retrieval device with the basket in a collapsed position within the sheath.
Figure 2B:
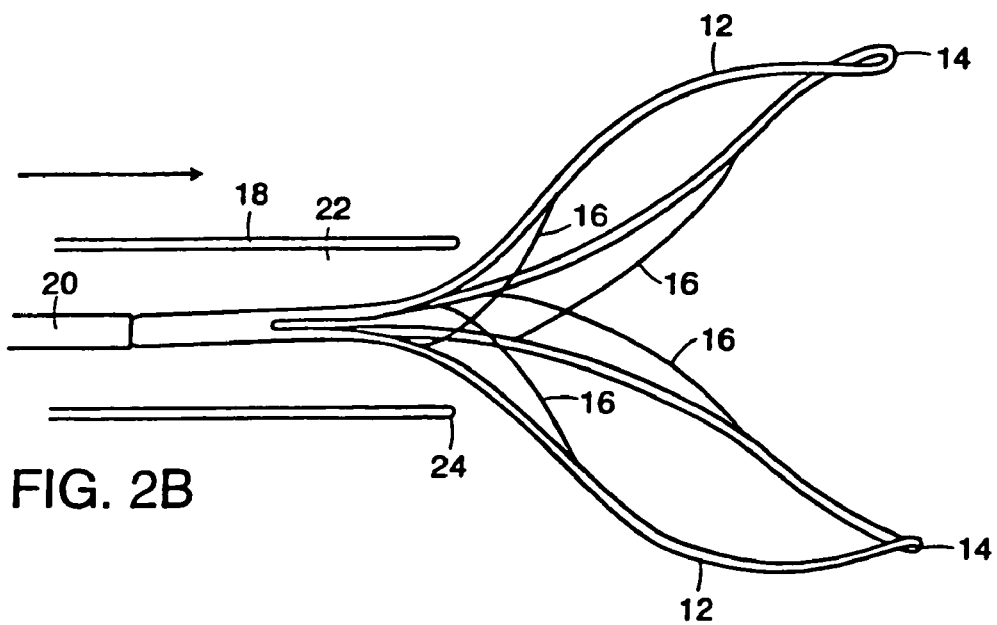
FIG. 2B is a plan view of the device of FIG. 2A with the basket in an open position and extended outside of the sheath.

Referring to FIG. 2A, in one embodiment of the invention, the fixed ends of the loops 15 at the basket base is operably attached to a first cable or elongate member 20 axially disposed within the lumen 22 of the sheath 18. The basket 10, when retained within the lumen 22 of the sheath 18, is in the collapsed position. In one embodiment, the sheath is made of an biologically inert, generally flexible material. Referring to FIG. 2B, advancing the first cable 20 in the direction of the arrow extends the basket 10 from the end 24 of the sheath 18. In this embodiment, the elasticity of the basket loops 12 causes the loops to part at their unattached ends 14 thereby moving the basket from a closed position to an open position. Alternatively, the sheath 18 is operably attached to an actuator 7 on the handle 9 and the sheath is axially moved over a stationery basket by actuating the actuator.

The basket 10 may assume any position between a closed position and an open position depending on the extent the basket has moved beyond the end of the sheath. For example, the basket may assume the intermediate position, illustrated in FIG. 2C. The ends 14 of the basket loops 12 may assume any position on an arc drawn by the unattached ends 14 of the basket loops 12 as the basket extends from fully out of the sheath to fully withdrawn within the sheath.

In the disclosed embodiment, the basket loops 10 are made from a metal material. For example, basket loop material can be specialty metals such as 455 custom stainless steel or NiTi ("Nitinol"). Alternatively the basket loops can be made from plastic, a composite, polymer, or other material. Also, the basket loops may be formed from laminations of the above materials. In the disclosed embodiment, the basket loops are made of flat wire (i.e., wire that is rectangular in cross section) that is about 0.003 to 0.005 inches thick, but may be of a round, D-shape, or other cross-sectional shape.

Referring to FIG. 3A, the basket loops can have an inner surface 11 that is designed to maximize grip on material. In one embodiment, as shown in FIG. 3B, at least a portion of the inner surface 11 is roughened by serrations or teeth. Roughening can also be achieved on the inner surfaces by etching, points, or a variety of other means. One or more of the basket loops may have such a rough inner surface, and it may cover all or a portion of one or more of the inner surfaces.

Figure 4A:
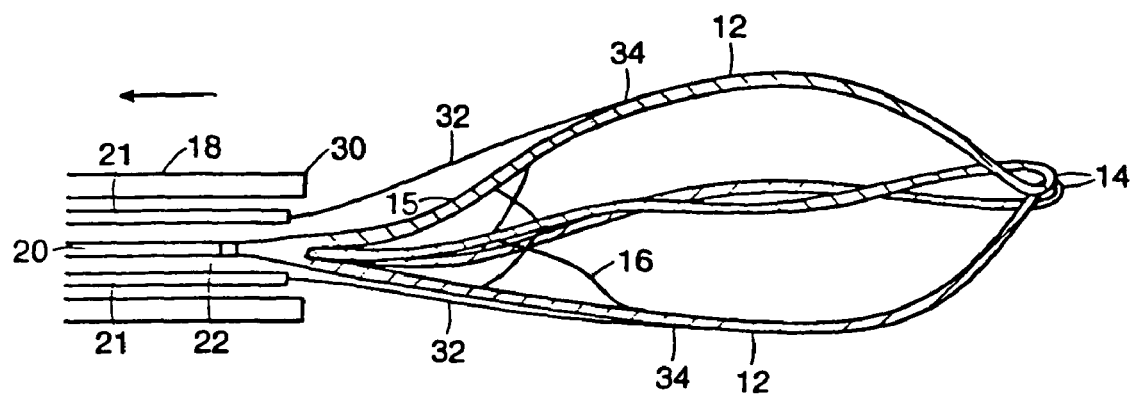
FIG. 4A is a plan view of a basket of the invention in the closed position illustrating second elongate members.

Referring to FIG. 4A, in an alternate embodiment, when the basket 10 is extended from the sheath 18, the basket maintains a closed position. In this alternate embodiment, an end of at least one wire 32 is operably attached to an intermediate portion 34 of at least one of the basket loops 12. The wire extends into the lumen 22 of the sheath 18 and is operably attached by its other end to a second cable or elongate member 21 disposed within the lumen 22 of the sheath 18. The second cable 21 may be disposed in the same or different lumens as the first cable 20. The wire 32 is kept taut by traction on the second cable 21 supplied by an actuating mechanism at the proximal handle of the device.

Figure 4B:
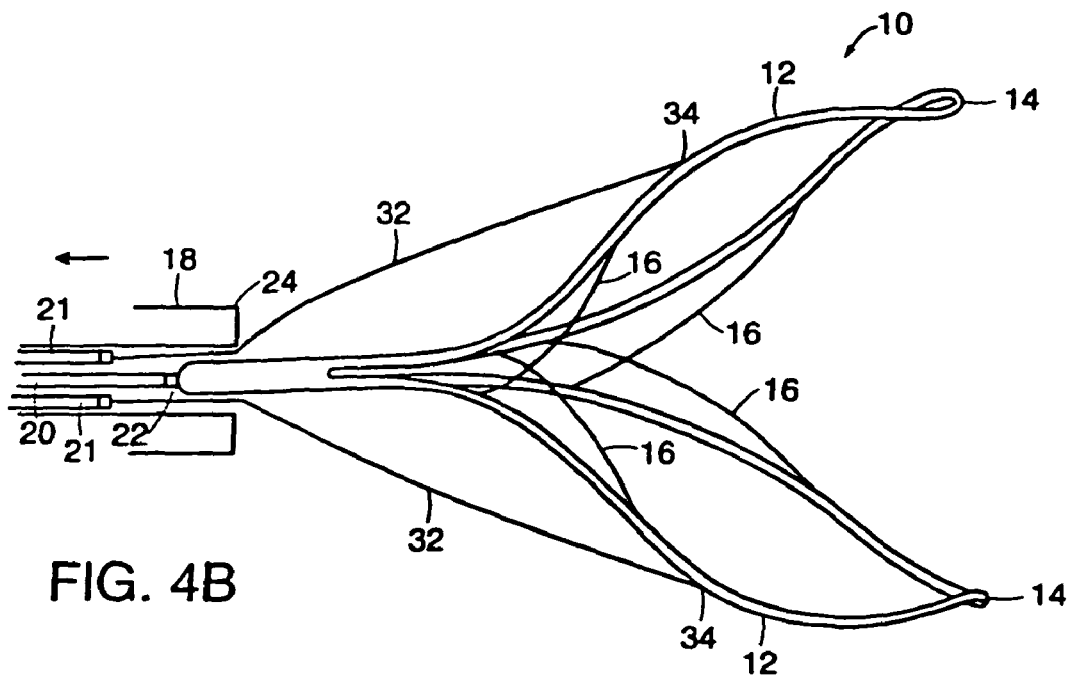
FIG. 4B is a plan view of a basket of the invention in the open position illustrating second elongate members.

With continued reference to FIG. 4A, when the second cable 21 is axially moved in the sheath lumen 22 in the direction indicated by the arrow, the tension on the wires 32 is increased and the ends 14 of the basket loops 12 move apart until the basket 10 is in an open position as illustrated in FIG. 4B. The position of the basket 10 may be additionally fine-tuned by axial movement of first cable 20. The ends 14 of the basket loops 12 may assume any position along an arc drawn by the ends 14 of the basket loops 12 depending on the degree of tension imparted to the wires 32 by the traction maintained on second cable 21 and first cable 20.

Figure 4C:
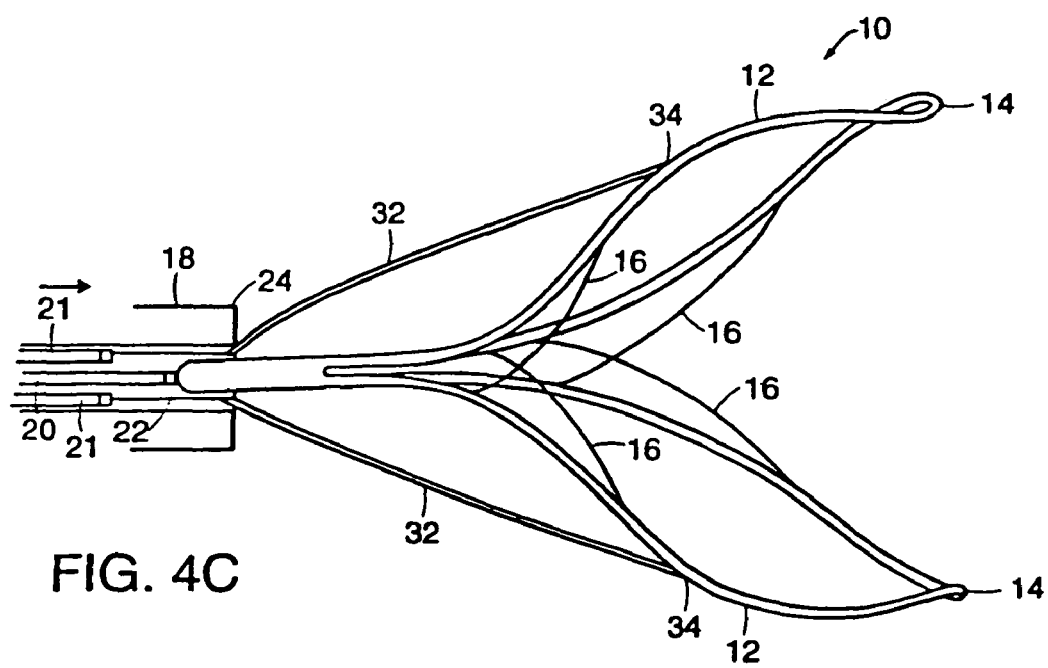
FIG. 4C is a plan view of a basket of the invention in the open position illustrating rigid second elongate members.
Figure 4D:
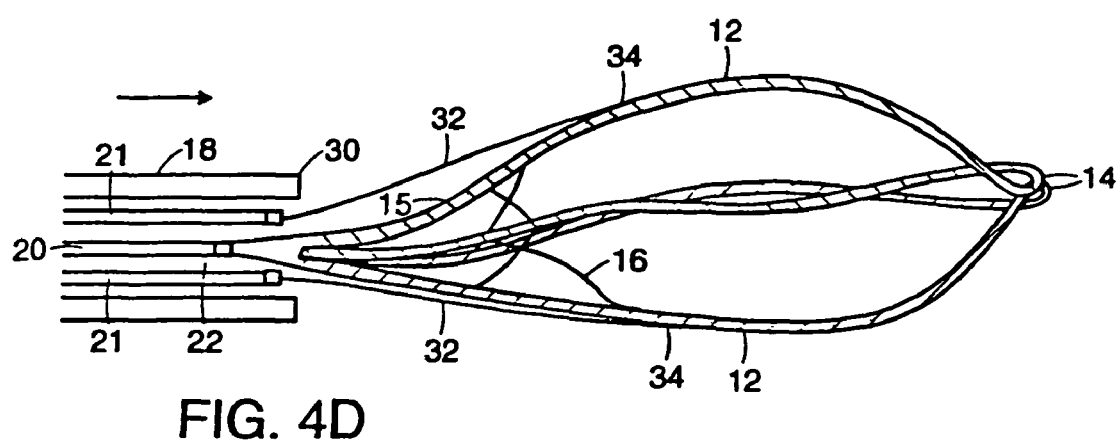
FIG. 4D is a plan view of a basket of the invention in the closed position illustrating rigid second elongate members.

Referring to FIG. 4C, in another embodiment of the invention, when the basket 10 is extended from the sheath 18, the basket 10 assumes an open position. In this embodiment, the wires 32 are formed of stiff material. To move the basket from an open to a closed position, the second cable 21 is advanced in the direction of the arrow. The stiff wires 32 push the basket loops ends 14 closer together thereby moving the basket from an open to a substantially closed position as shown in FIG. 4D. Further fine adjustment to the basket can be made by axial movement of first cable 20.

In other embodiments of the invention, the device includes two or more basket loops and at least one wire operably attached to at least one of the two or more basket loops.

Figure 5A:
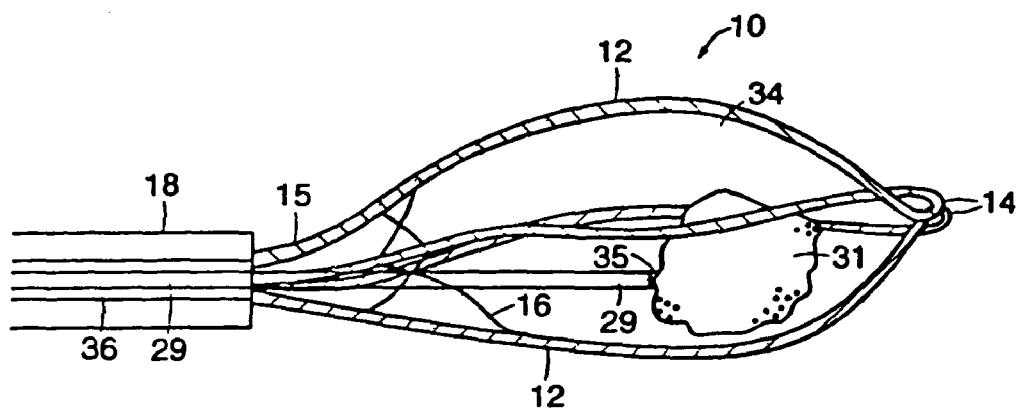
FIG. 5A is a plan view of an embodiment of a basket according to the invention including a lithotriptic device.

Referring to FIG. 5A, in another embodiment of the invention, a channel 36 is longitudinally disposed within the sheath 18 and extends through the fixed end 15 of the basket loops into the lumen 34 of the basket 10. A ram-rod 29 or other lithotriptic device such as, for example, a laser, is longitudinally disposed in the channel 36. In operation, a stone 31 is captured in the lumen 34 of the basket 10. The ram-rod 29 is advanced in the channel beyond the fixed ends 15 of the basket loops and into the lumen 34 of the basket 10 until the end 35 of the ramrod 29 abuts the stone 31. The stone 31 is then fragmented by lithotripsy. The fragmented stones 31 are withdrawn from the tract while encapsulated in the basket.

Figure 5B:
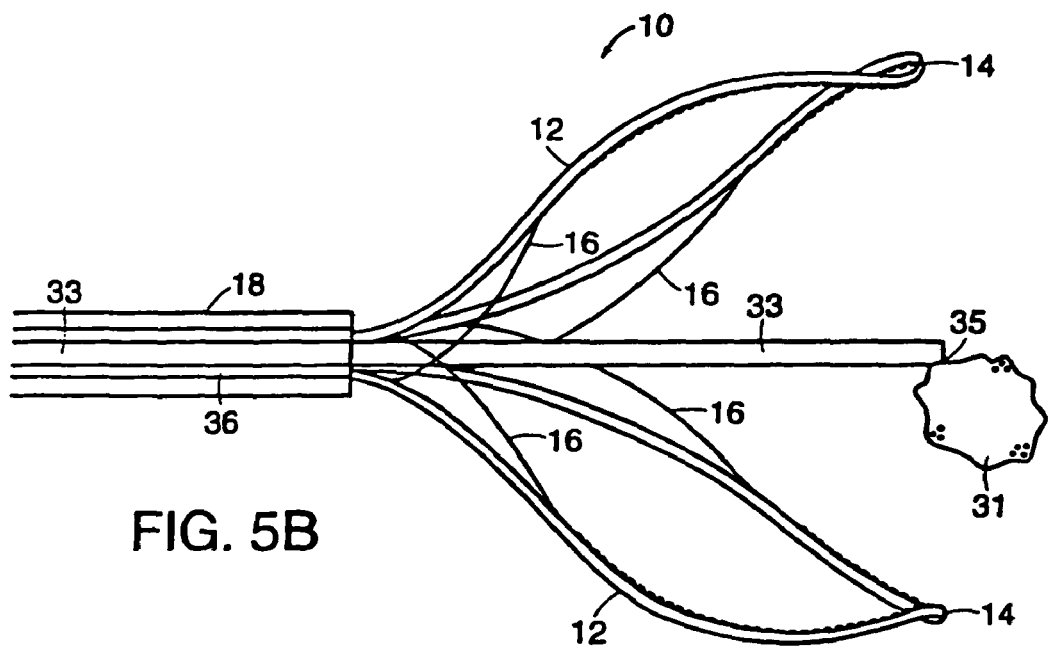
FIG. 5B is a plan view of an embodiment including a push rod.

Referring, to FIG. 5B, in an alternate embodiment of the invention, after fragmentation of the stone, or under circumstances in which it is desirable to release the stone from the basket, the basket 10 is moved from the closed position to the open position. A push rod 33 disposed within the channel 36 is advanced into the lumen 34 of the basket until the end 35 of the push rod 33 contacts the stone or stone fragment 31. The push rod 33 is advanced further into the lumen 34 of the basket 10 until the stone or stone fragment 31 is pushed out of the basket lumen 34 through the parted ends 14 of the basket loops 12.

Figure 6:
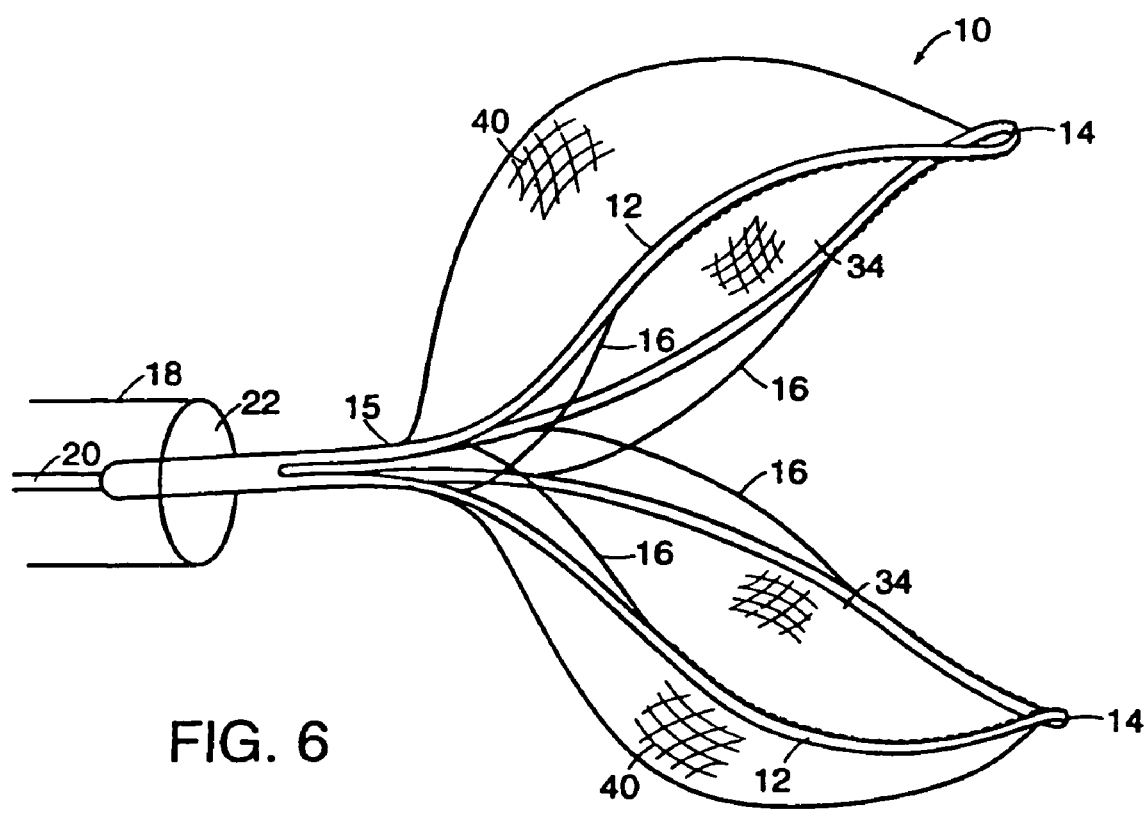
FIG. 6 is a plan view of a device having a mesh disposed within the basket loops.

Referring to FIG. 6, in yet another embodiment of the invention, the basket loops 12 have a membrane or mesh material 40 disposed within the loops 12. The basket loops 12 serve as a frame to support the mesh or membrane. The mesh or membrane 40 is attached to the wire loop frame by any means known to one skilled in the art. In one embodiment, as illustrated in FIG. 6, the mesh or membrane 40 of the loops 12 form a concavity so that the lumen 34 of the basket is a pocket or is cup-shaped. The mesh or membrane 40 can be formed of polymer, membrane, wire, metal, mesh, film, cloth, fabric, textile, woven material, etc.

Figure 7A:
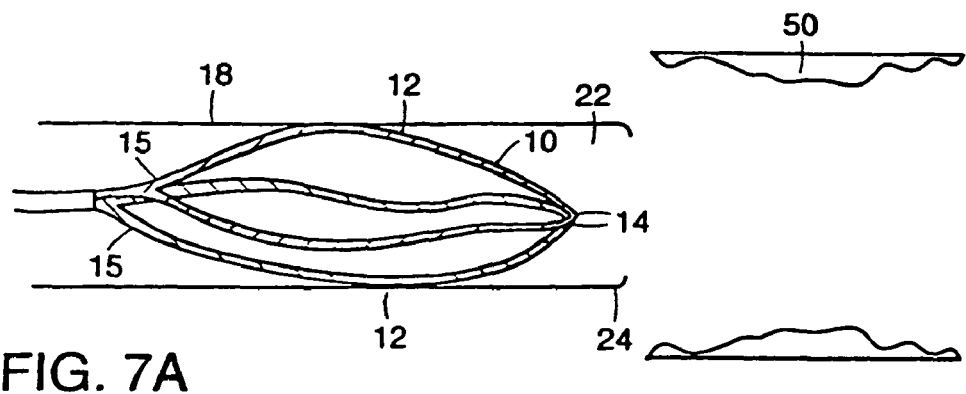
FIGS. 7A-7D are diagrammatic representations of a clinical application of the device of FIGS. 2A, 2B, and 2C.
Figure 7B:
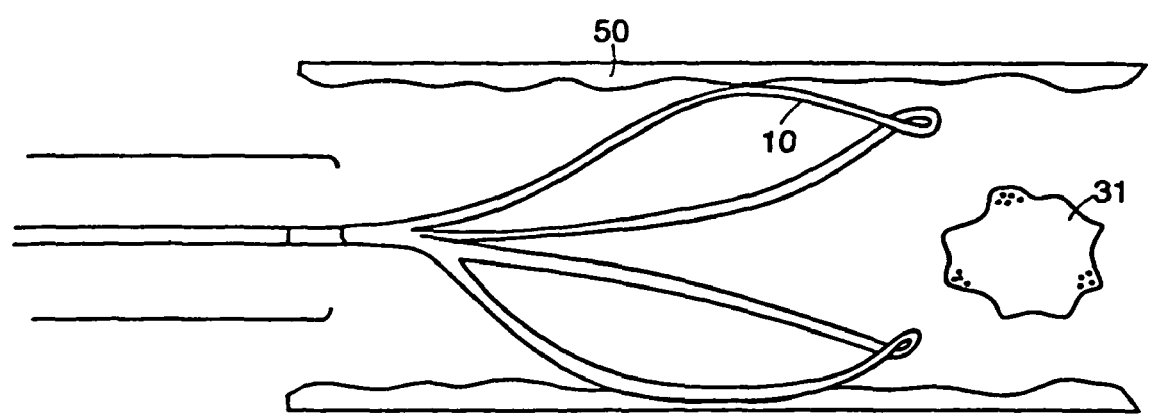
Figure 7C:
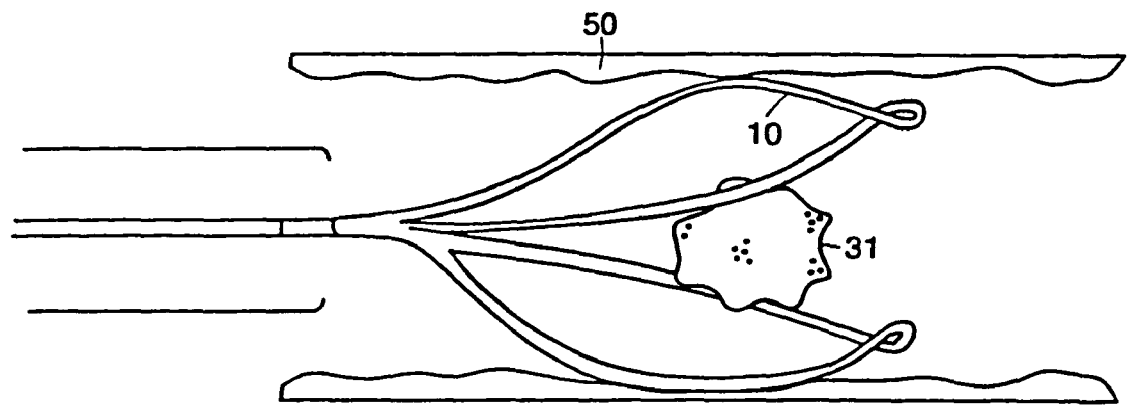
Figure 7D:
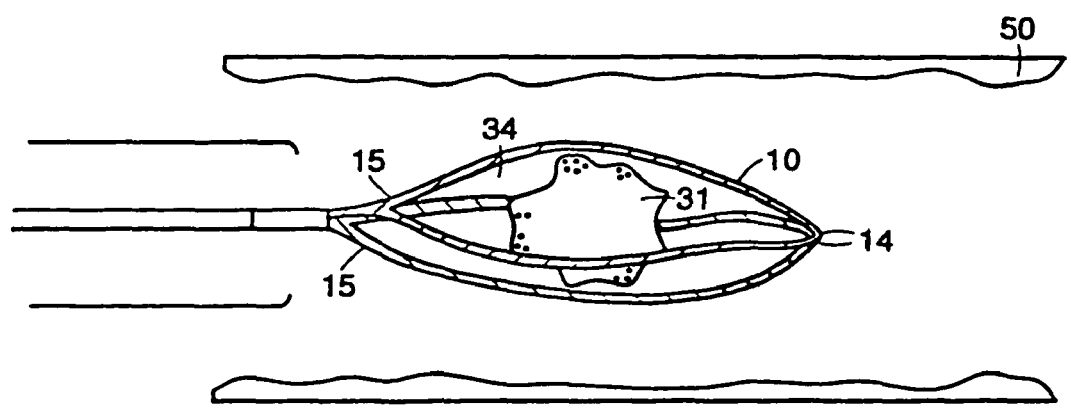

In operation, referring to FIG. 7A, the retrieval device is inserted into a tract 50 of the body to retrieve biological material, for example, a stone in the gall bladder, biliary tree, ureter, is kidney, or urethra. The end of the device 24 is inserted into the tract 50 while the basket 10 is collapsed and enclosed within the sheath 18. Referring to FIG. 7B, the basket 10 is advanced in the body tract 50 until the end of the basket 24 approaches the stone 31. As the basket approaches the stone 31, the basket 10 is extended out of the sheath and moved from a collapsed position to an open or intermediate position. The method of opening and closing the basket does not substantially alter the operation of the device in capturing a stone within a tract. Referring to FIG. 7C, the basket 10 is advanced further into the body tract 50 until the stone 31 is captured by end-encapsulation. End-encapsulation occurs when the stone 31 passes between the parted unattached ends 14 of the open basket 10. Referring to FIG. 7D, after the stone 31 is positioned within the lumen 34 of the basket 10, the basket 10 is returned to a closed position. The unattached ends 14 of the basket loops 12 are substantially juxtaposed entrapping the stone 31 within the basket 10. It is not essential to the operation of the basket that the unattached ends 14 of the basket loops 12 actually meet. For particularly large stones, for example, the diameter of the stone will prevent juxtaposition of the unattached ends of the basket. However, the essential feature of successful end-encapsulation for stone removal is sufficient contact between the inner surface of the basket loops with the stone surface so that the stone does not inadvertently slip out of the basket. The retrieval device with the entrapped stone is withdrawn from the body tract.

Figure 8A:
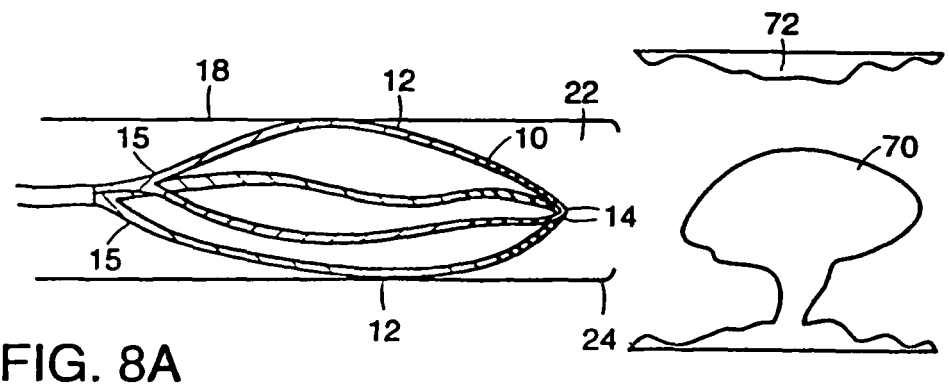
FIGS. 8A-8D are diagrammatic representations of another clinical application of a device according to the invention wherein the basket loops excise a tissue.
Figure 8B:
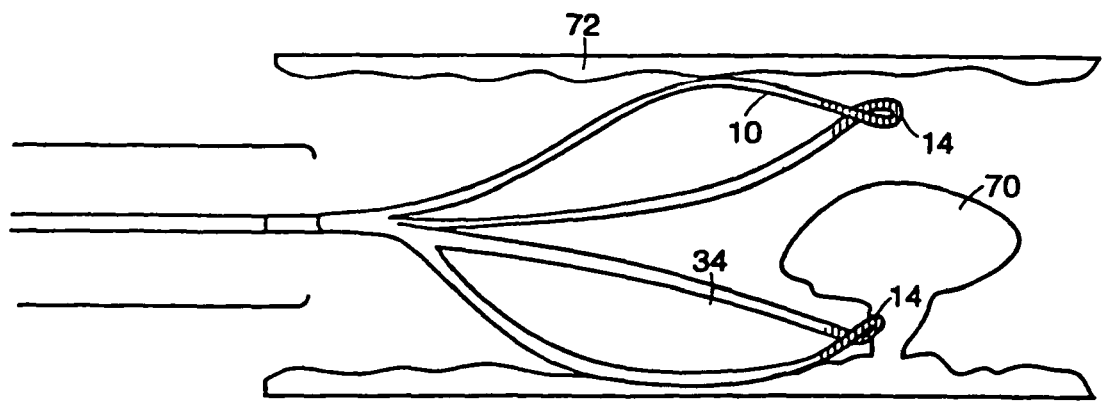
Figure 8C:
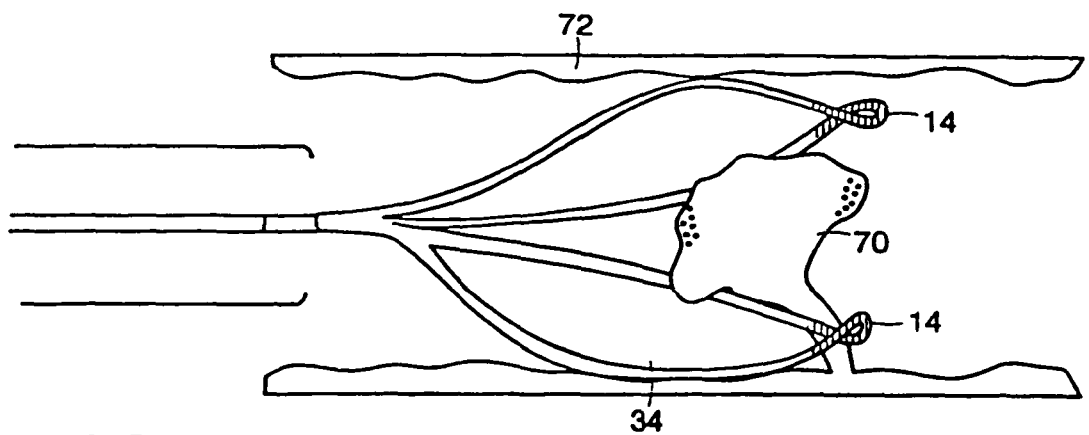
Figure 8D:
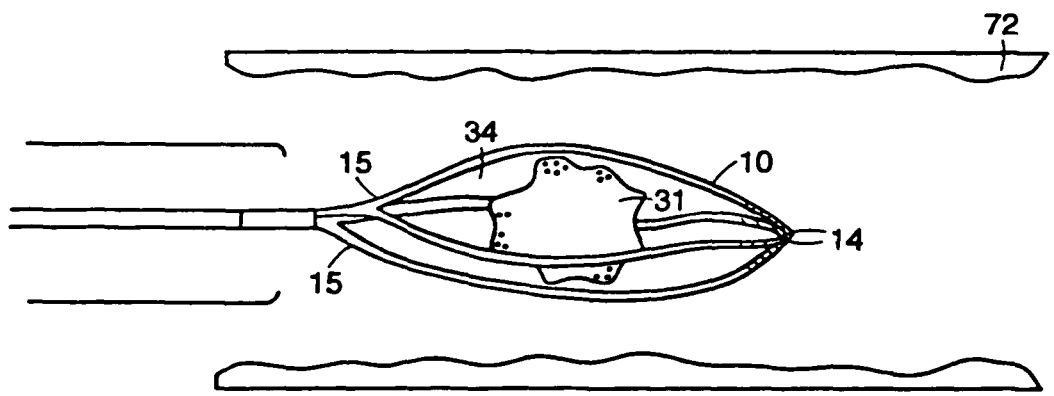

Referring to FIG. 8A, in yet another embodiment of the invention, the basket loops may be used to excise tissue (i.e., perform a biopsy procedure), for example a polyp 70 in the lumen of the gastrointestinal tract 72. An advantage of this embodiment of the invention is that the polyp 70 is preserved in the basket lumen following polypectomy in a condition suitable for subsequent pathological examination. In one embodiment, the basket loops are energized, for example, at the unattached ends 14 of the basket loops 12. In operation, as shown in FIG. 8A, the retrieval device is advanced into the lumen of the gastrointestinal tract 72, preferably under endoscopic guidance, until the basket 10 approaches the polyp 70. The polyp is end-encapsulated when the basket 10, in the open position, is advanced over the polyp as illustrated in FIG. 8B. The polyp 70 is captured within the basket lumen 34 as shown in FIG. 8C, and the basket 10 is moved to a substantially closed position. Sufficient energy by any means known to one skilled in the art is applied to all portions of the basket loops 12 such as the unattached ends 14 of the loops. Alternatively, the basket loops may have a cutting surface to permit excision of the polyps. Sufficient energy is applied to the basket loops to separate the polyp 70 from its stalk. Referring to FIG. 8D, the polyp 70, detached from the body, drops into the basket lumen 34. The polyp 70 within the basket lumen 34 is withdrawn from the gastrointestinal tract 72. The polyp may be removed from the basket for subsequent pathological analysis.

Figure 9A:
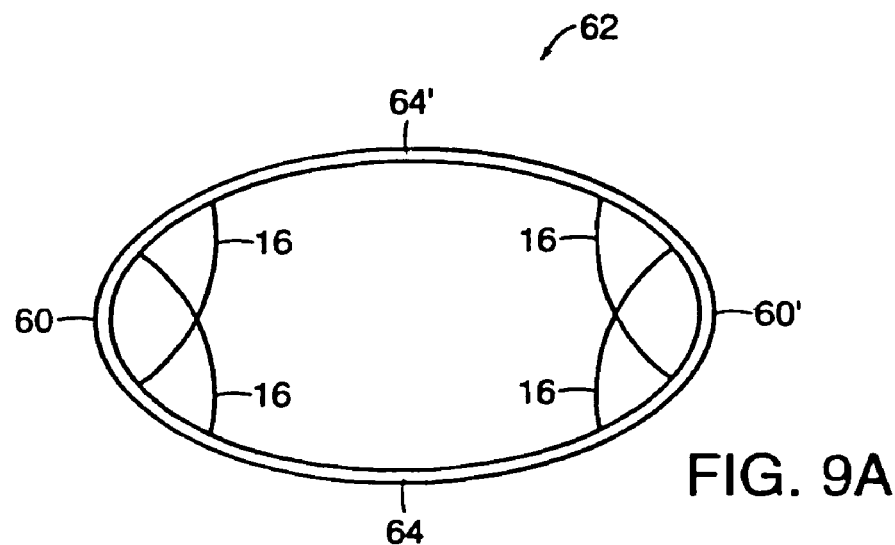
FIGS. 9A-9E illustrate a method for constructing a basket according to the invention.

In another aspect of the invention, the basket loops are constructed from a single piece of material. Referring to FIG. 9A, a frame 62 is created from a unitary piece of material. In one embodiment, the frame can be substantially oval and symmetrical with two oppositely disposed ends, 60 and 60', two loop members 64 and 64', and support members 16. The frame 62 is removed from a single piece of substantially flat material by cutting, etching, stamping, extruding, or removing by any other method known to one skilled in the art for constructing a template from a single piece of material. Referring to a particularly preferred embodiment of the invention shown in FIG. 9B, following construction of the frame 62, the ends 60, 60' of the frame 62 are brought together to superimpose the ends on one another as indicated by the arrows in the side view of the frame illustrated in FIG. 9C. The ends 60, 60' are then secured to one another thereby forming the three dimensional basket structure illustrated in FIG. 9D with two loops. That is, the members 64, 64' become the basket loops, as illustrated in FIG. 9D. The basket is shaped by cold deformation or heat shaping.

Figure 9B:
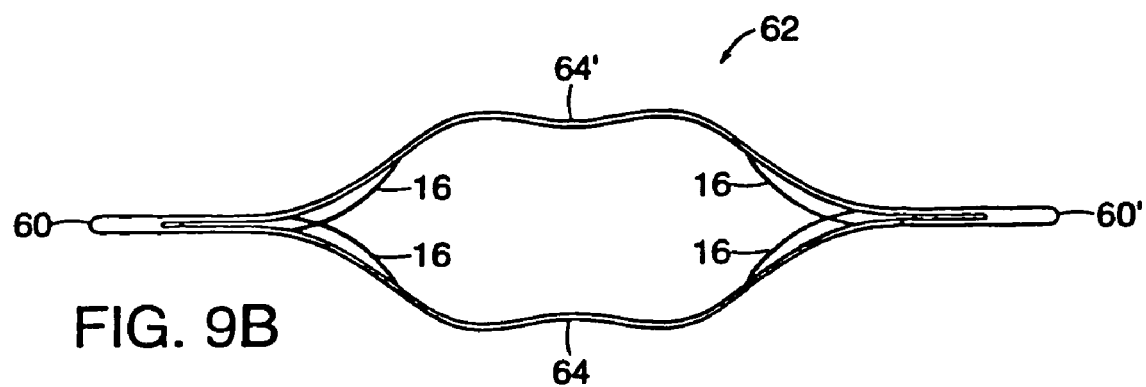
Figure 9C:
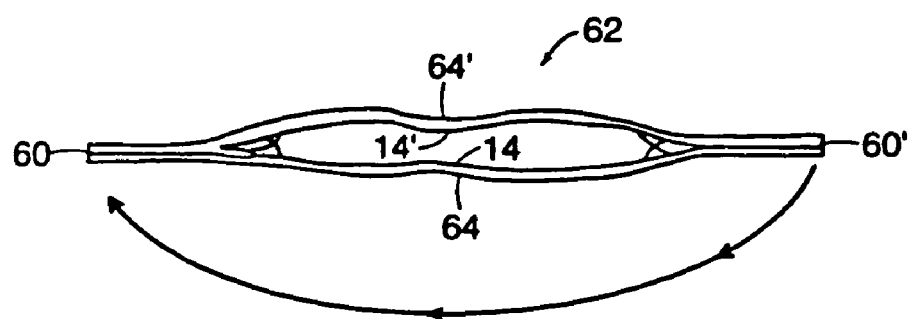
Figure 9E:
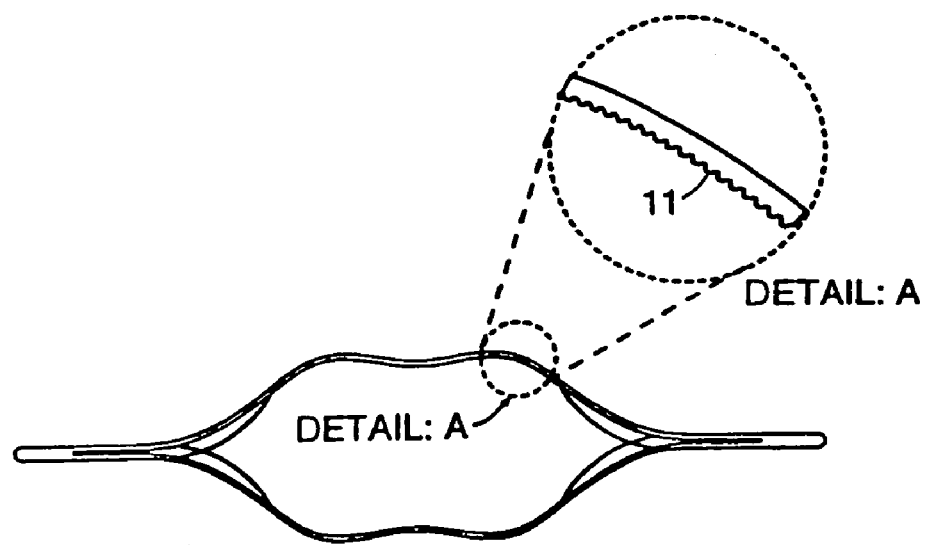
Figure 9D:
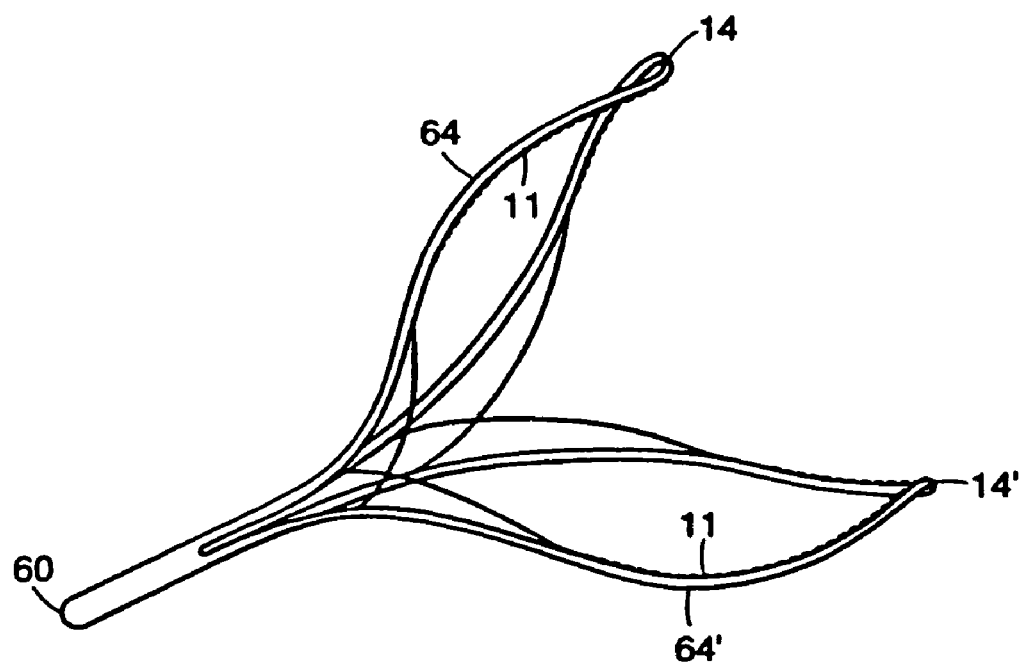

In another embodiment, the retrieval basket 10 illustrated in FIG. 9D, made from the frame illustrated in FIGS. 9B and 9C, is joined to an elongated member as illustrated in FIG. 9F. In this embodiment, a wire 104 includes a first portion 102, an intermediate portion 102', and a second portion 102". Wire 104 is passed in a proximal to distal direction through the lumen 101 of a base cannula 100, then, between the proximal ends of the two loops 12, 12' at the base 15 of the retrieval basket 10, and back through the lumen 101 of cannula 100 in a distal to proximal direction. The intermediate portion 102' of the wire is positioned between the loops 12, 12'. The wire loops 12, 12' including proximal ends 16 are snugged up to the base cannula 100 by pulling on the first and second portions 102, 102' of the mandril wire 104 in a proximal direction indicated by the arrow in FIG. 9F to form the retrieval basket 10, base cannula 100, and elongated member 20 shown in FIG. 9G. Adhesive may be added to the base cannula 100.

In an alternate embodiment of the invention, a two, three, four, or more loop basket is formed from a unitary piece of material by cutting, stamping, or etching a frame from a unitary piece of material, or by molding or extruding a frame. For example, referring to FIG. 10B, a frame 62 is substantially flat having three loop members, 108a, 108b, 108c, and three joining members 114a, 114b, 144c connecting the three loop members 108a, 108b, 108c to define an aperture 112. A joining member is any segment on the frame that is joined to or superimposed on at least one another segment in the frame to form the loops of the basket. A joining member may be located at the ends of loop members, or anywhere along the length of a loop member. A joining member may be an enlargement, or extension of a loop member. In a three loop embodiment of a retrieval basket 10, illustrated in FIG. 10A, the frame 62, illustrated in FIG. 10B, has three joining members 114a, 114b, and 114c, and is folded to superimpose the joining members 114a, 114b, 114c on one another. By superimposing the joining members on one another, the loop members 108a, 108b, 108c are caused to form opposing loops 12 that extend away from the joining members to form the basket 10 illustrated in FIG. 10A. Further shape refinements of the basket 10 are accomplished by cold deformation or heat shaping. The joining members 114a, 114b, and 114c are gathered together to form the fixed end 15 of the basket 10. The midsection of each of the loop members 108a, 108b, and 108c forms the free end 14 at the apex of each corresponding loop 12. In a four loop embodiment of a basket illustrated in FIG. 10D, the frame 62, illustrated in FIG. 10E has four joining members 114a, 114b, 114c, and 114d and four loop members 108a, 108b, 108c, and 108d, and is folded to form the basket 10 illustrated in FIG. 10D . The number of joining members 114 in a frame 62 corresponds to the number of loops 12 in the basket 10.

The two, three, four, or more loop basket can be removed from a single piece of flat material, as illustrated in FIG. 10C, for a three loop frame 62, or from a single piece of flat material illustrated in FIG. 10F, for a four loop frame 62. Alternatively, the two, three, four, or more loop basket of the invention can also be formed from a frame 62 constructed from one or more wires 116. As illustrated in FIG. 10G, for example, a frame 62 is featured for a three loop basket. The frame 62 has three wires 116a, 116b, 116c. Each end of each of the three wires 116a, 116b, 116c is attached to a different end of at least one other wire to form the frame illustrated in FIG. 10G. In an alternate method of making a three loop basket, two wires 116a, 116b can be used to form the frame 62 illustrated in FIG. 10H. In a two wire configuration for a three loop frame, one wire 116a is bent to form joining member 114a. Each end of wire 116b is joined to a different end of wire 116a.

Figure 10I:
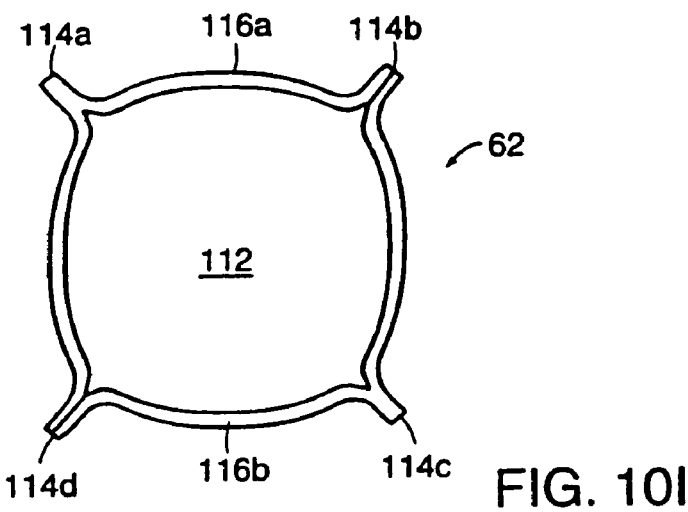
FIG. 10I illustrates an embodiment of a shape according to the invention for forming the basket illustrated in FIG. 10D.
Figure 10J:
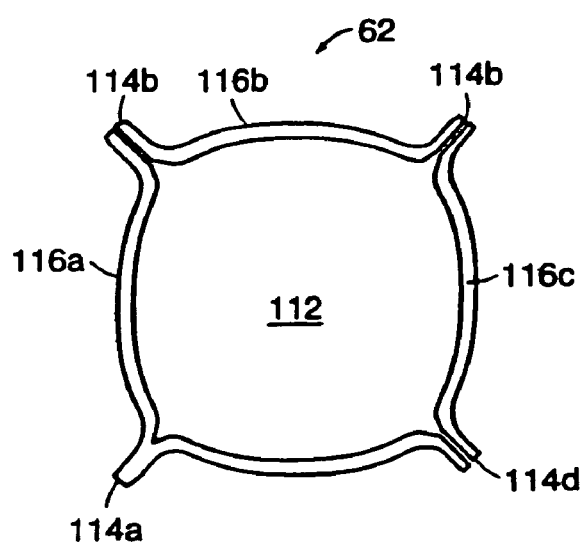
FIG. 10J illustrates an embodiment of a shape according to the invention for forming the basket illustrated in FIG. 10D.

In a two wire configuration for a four loop frame, illustrated in FIG. 10J, wire 116a is bent to form joining member 114a and wire 114b is bent to form joining member 114c. Each end of each of the wires 116a, 116b is joined to a different end of the other wire. The remaining two joining members 114*b*, 114*d* of the four loop frame 62 are formed where the wires are joined to one another.

Featured in FIG. 10J, three wires 116*a*, 116*b*, 116*c* can be used to form a four loop frame 62. For example, one wire 116*a* is bent to form joining member 114*a*. Each end of each of the three wires 116*a*, 116*b*, 116*c* is joined to a different end of another wire to form the four loop frame 62 illustrated in FIG. 10J. Where the three wires 116*a*, 116*b*, 116*c* are joined is where remaining three joining members 114*b*, 114*c*, 114*d* of the frame 62 are formed.

Figure 10K:
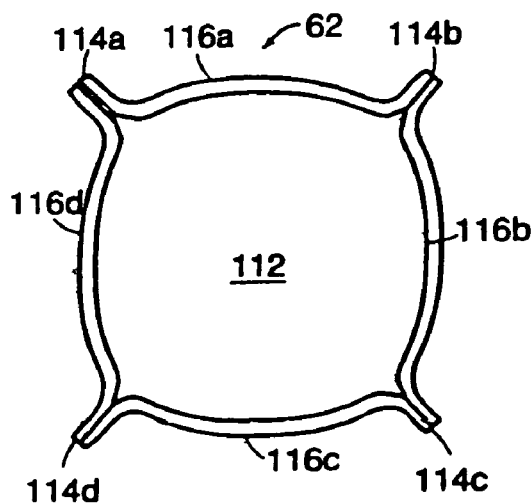
FIG. 10K illustrates an embodiment of a shape according to the invention for forming the basket illustrated in FIG. 10D.

Featured in FIG. 10K, four wires 116*a*, 116*b*, 116*c*, 116*d* can be used to form a four loop frame 62. For example, each end of each of the four wires 116*a*, 116*b*, 116*c*, 116*d* is joined to a different end of another wire to form the four loop frame illustrated in FIG. 10K. Where the four wires 116*a*, 116*b*, 116*c*, 116*d* are joined is where the four joining members 114*a*, 114*b*, 114*c*, 114*d* of the frame 62 are formed.

Figure 10L:
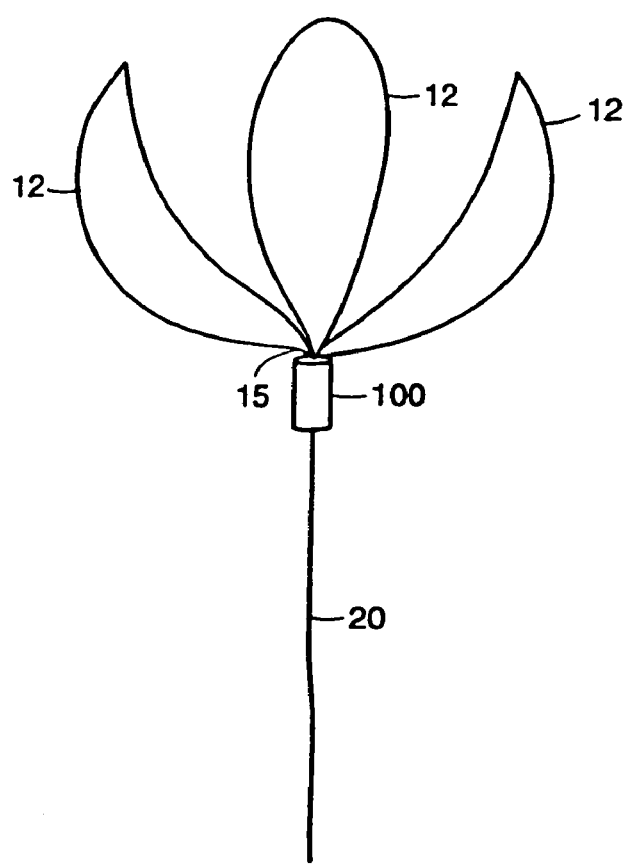
FIG. 10L illustrates an embodiment of a three loop basket joined to an elongated member according to the invention.
Figure 10M:
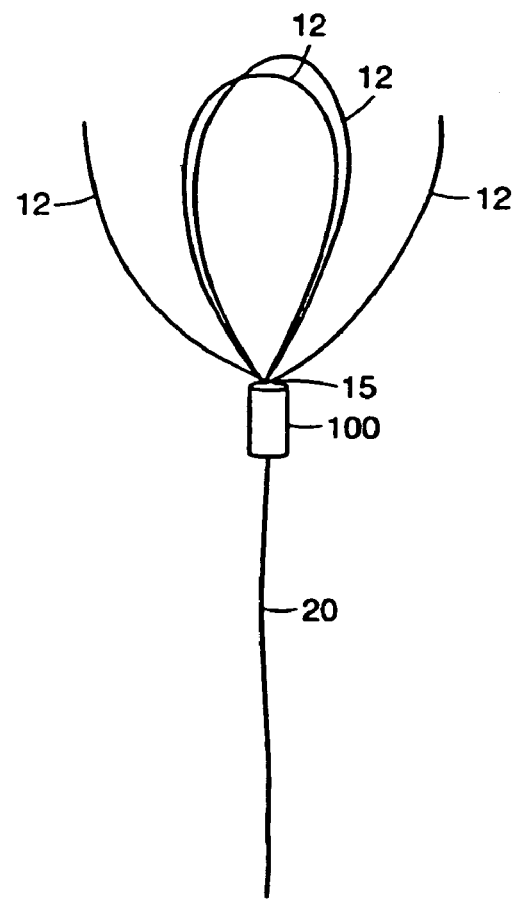
FIG. 10M illustrates an embodiment of a four loop basket joined to an elongated member according to the invention.

The frame 62 illustrated in FIGS. 10B, 10C, and 10E-10K, is folded to form the three, four, or more loop basket 10 illustrated in FIGS. 10A and 10D, by bringing together the joining members 114 of the frame 62 to form the fixed end 15 at the base of the basket 10. In the three loop embodiment illustrated in FIG. 10L, and the four loop embodiment illustrated in FIG. 10M, the fixed end 15 of the basket base is joined to an elongated member 20, for example, in a base cannula 100 by crimping, gluing, or soldering by some other method known to the skilled person.

The joining members are used merely to enhance the ease by which the baskets are made. A frame such as a circle, oval, rectangular, or, any polygonal frame could be used to make the retrieval assembly of the invention.

Figure 11A:
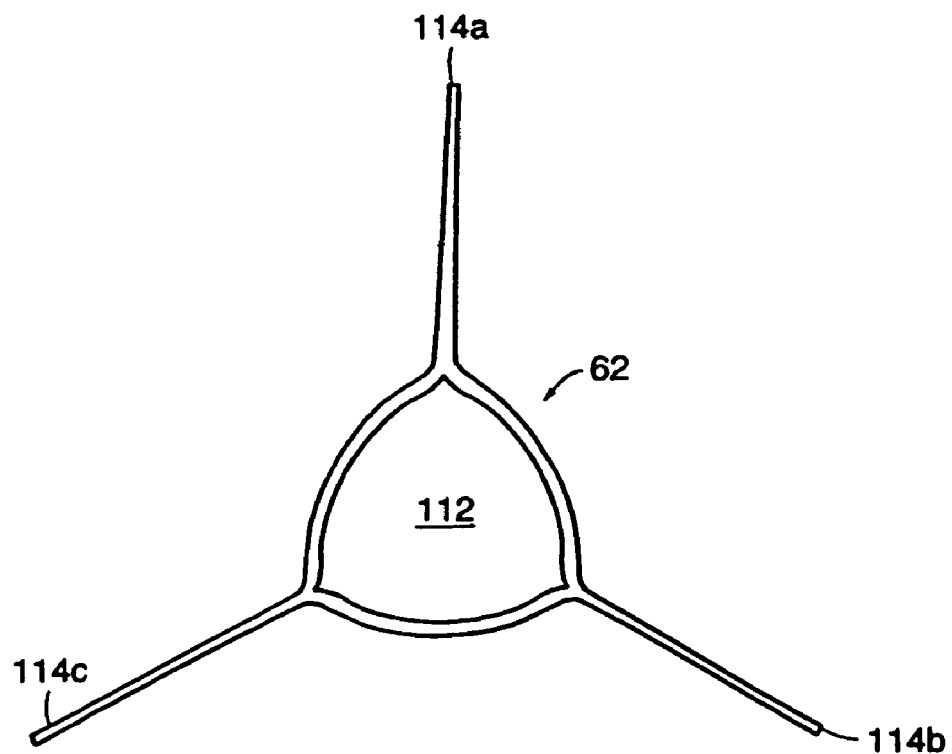
FIG. 11A illustrates an embodiment of a shape for the three loop basket illustrated in FIG. 11B according to the invention.
Figure 11B:
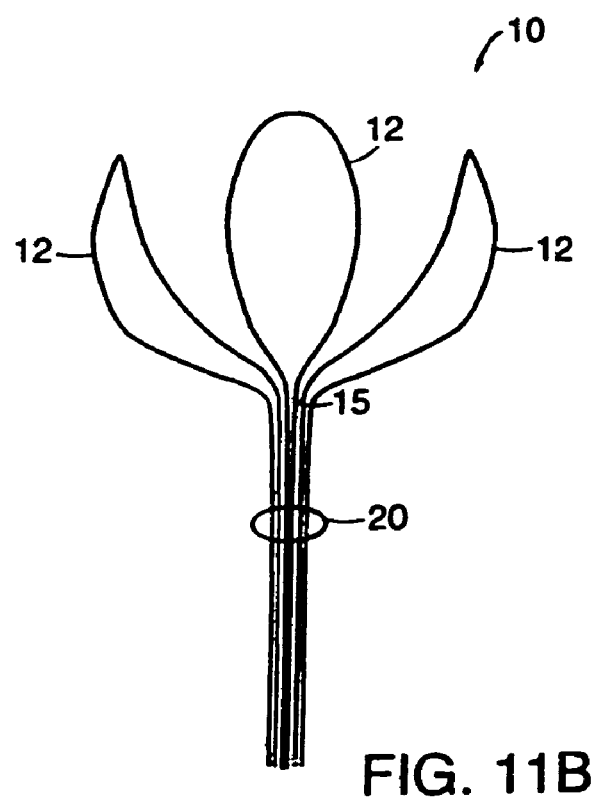
FIG. 11B illustrates an embodiment of a three loop basket formed from the shape illustrated in FIG. 11A according to the invention.

In yet another embodiment, illustrated as frame 62 for a three loop basket in FIG. 11A, the joining members 114*a*, 114*b*, 114*c* of the frame 62 are elongated. When the frame 62 is folded to form the basket 10 illustrated in FIG. 11B, the elongated joining members 114*a*, 114*b*, 114*c* are gathered together to form the elongated member 20.

An additional feature can be added to the two loop basket embodiment to form a basket with opposing hemi-basket structures 110*a*, 110*b* as illustrated, for example, in FIG. 12A. To form a hemi-basket, a back stay 116*c* extends in a plane perpendicular to the plane of the face of the loop formed by members 116*a* and 116*b*. The ends of members 116*a*, 116*b*, 116*c* are gathered together to form the base 15 of the hemi-basket. The proximal or fixed end 15 at the base of opposing hemi-baskets 110*a*, 110*b* is joined to the distal end of an elongated member 20. The hemi-baskets 110*a*, 110*b* reciprocally open and close in a clam shell fashion by axial movement of the elongated member 20 to extend and retract the basket 10 within the sheath lumen 22. Alternatively the sheath 18 reciprocally moves axially over the basket 10 at the distal end of the elongated member 20. By either method of moving the basket 10 relative to the sheath 18, the opposing hemi-basket structures 110*a*, 110*b* are closed when retracted into the sheath lumen 22 and open when extended beyond the end of the sheath 18.

The basket 10 illustrated in FIG. 12A is formed from a substantially T-shape configuration 62, including three members 108*a*, 108*b*, 108*c*, such as the configuration 62 shown in FIG. 12B. Each member 108*a*, 108*b*, 108*c* has a free end. One member 108*a* is perpendicular to the other members 108*b*, 108*c*. The T-shape configuration 62 is stamped, etched, or cut from a single piece of material to form three members 108*a*, 108*b*, 108*c*.

Alternatively, two or more wires 116 can be twisted together to form the T-shape configuration 62. For example, as illustrated in FIG. 12C, two wires 116*a*, 116*b* are twisted together to make one twisted member 108*a* and two untwisted members 108*b* and 108*c* of the T-shape configuration 62. In FIG. 12D, two wires 116*a*, 116*b* are used to form the T-shape configuration 62. One wire 116*a* of the two wires is twisted on itself to form one twisted member 108*a* of the T-shape, while the other wire 116*b* passes through an end of the twisted wire 116*a* to form the other two members 108*b*, 108*c* of the T-shape configuration. Alternatively, shown in FIG. 12E, three wires 116*a*, 116*b*, 116*c* are used to form a T-shape configuration 62 with three twisted members. To make the T-shape configuration 62 illustrated in FIG. 12E, a two wire 116*a*, 116*b* T-shape configuration like the configuration 62 illustrated in FIG. 12C and discussed in the corresponding text, is formed initially. A third wire 116*c* is twisted with the remaining untwisted portion of wires 116*a*, 116*b* to form the T-shape configuration with twisted wires in each of the three members 108*a*, 108*b*, 108*c* illustrated in FIG. 12E.

Figure 12J:
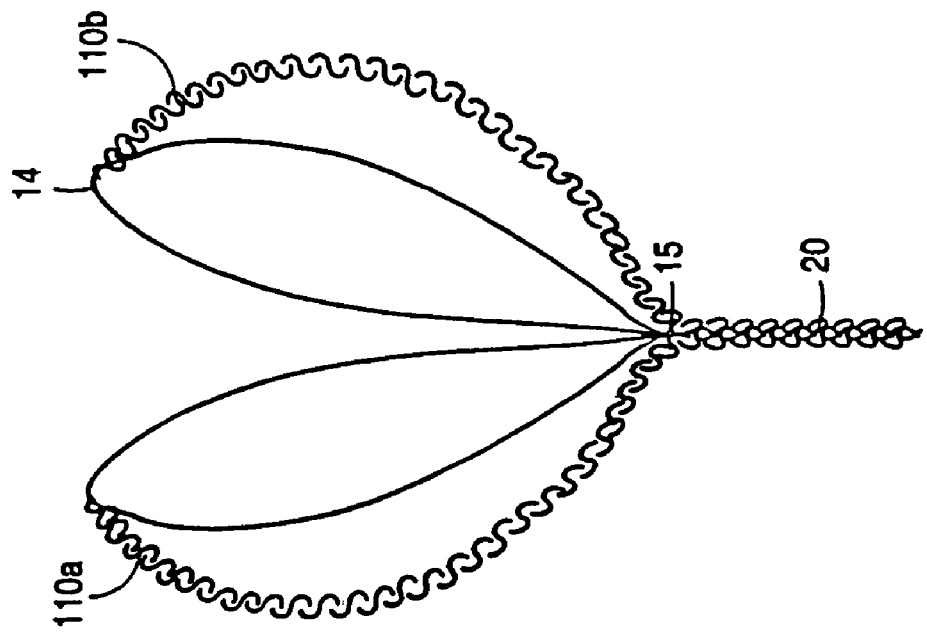
FIG. 12J illustrates another embodiment of a retrieval basket and elongated member according to the invention.
Figure 12I:
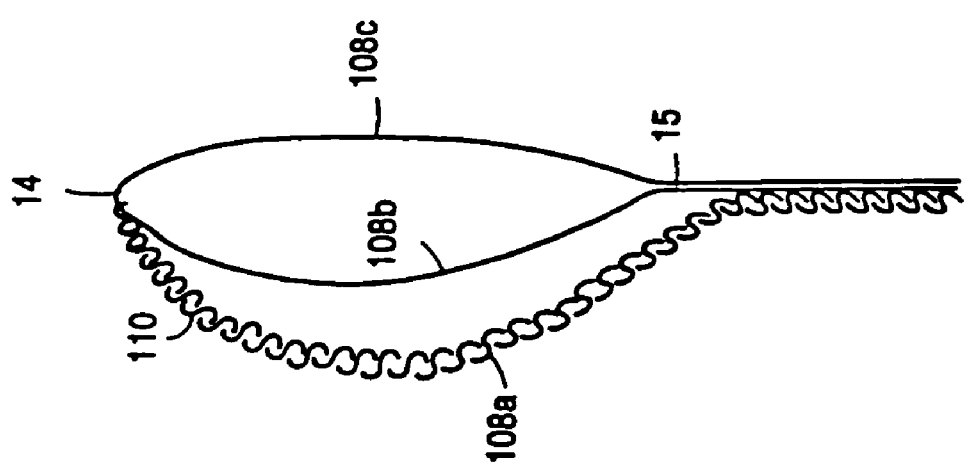
FIG. 12I illustrates another embodiment of a hemi-basket used to form the basket in FIG. 12A.

To form the hemi-baskets 110*a*, 110*b* of the retrieval basket 10 illustrated in FIG. 12A, two 108*b*, 108*c* of the three members 108 illustrated in FIG. 12G are folded to form a loop with the free ends of the two members 108*b*, 108*c* gathered together. The distal or closed end 14 of the loop is formed at the intersection of the three members 108*a*, 108*b*, 108*c* of the T-shape configuration 62. The third member 108*a*, that runs perpendicular to the other two members, is folded down to form a back stay as illustrated in FIG. 12I. The end of member 108*a* is gathered together with the ends of members 108*b*, 108*c* to form the fixed end 15. Further frame modifications are accomplished by cold deformation or heat shaping. When two of the hemi-basket structures 110*a*, 110*b* are opposed, a clam shell structure results as illustrated in FIG. 12H. The free ends 15 of the loops and back stay can be attached to an elongated member 20 to form the clam shell retrieval assembly illustrated in FIG. 12A. Alternatively, the free ends of the members of the T-shaped configuration can be gathered or twisted together as shown in FIG. 12J to form the elongated member 20.

A retrieval basket including two hemi-basket structures can be formed from the frame illustrated in FIG. 12F. In this embodiment, the frame 62 is removed from a single piece of material. The frame is folded to form two hemi-baskets by superimposing member 21*a* on member 21*b* and bending member 120*a* to make the back stay of one hemi-basket, and bending member 120*b* to make the back stay of the other hemi-basket. Thus the apex of the two loops of the hemi-baskets are formed from 14*a* and 14*b*.

Figure 13C:
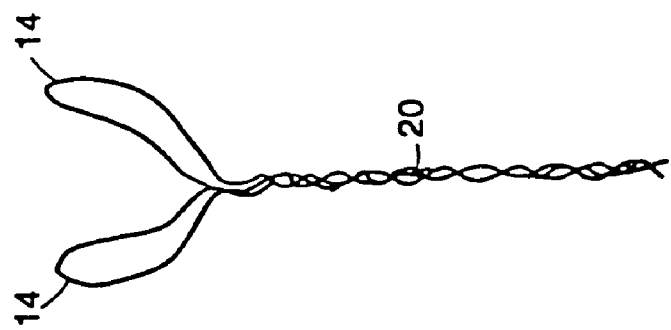
FIG. 13C illustrates an embodiment of a two loop basket and elongated member.
Figure 13B:
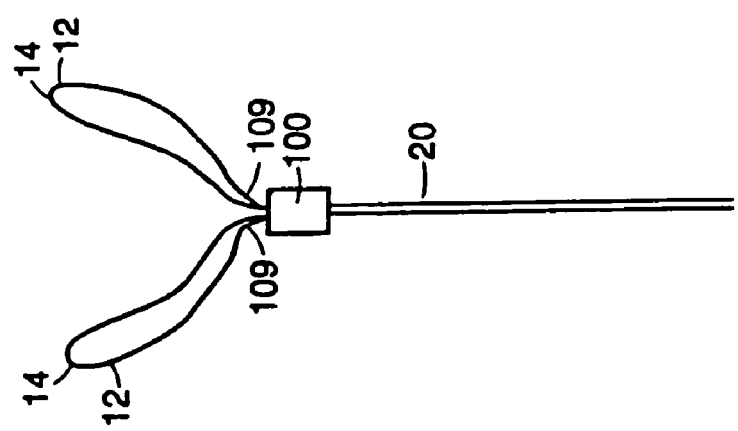
FIG. 13B illustrates an embodiment of a two loop basket and elongated member formed in the step illustrated in FIG. 13A according to the invention.
Figure 13A:
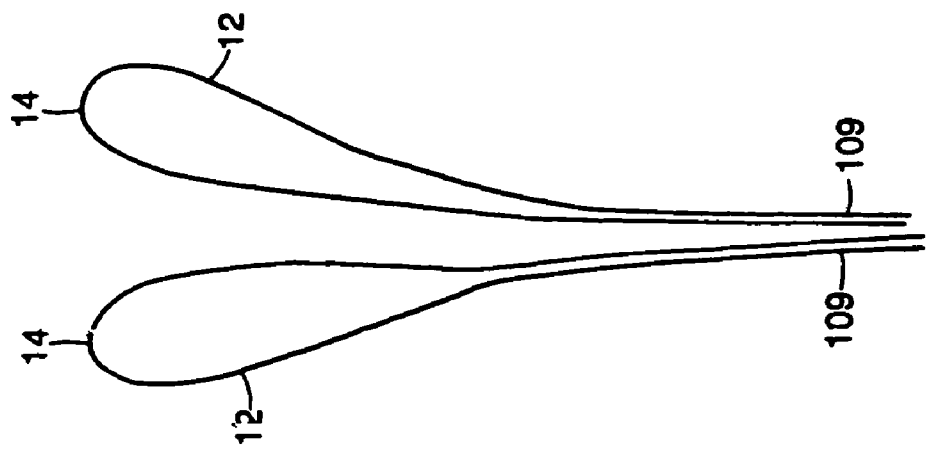
FIG. 13A illustrates another embodiment of an intermediate step for forming a two loop basket according to the invention.

Another method, according to the invention, for forming a retrieval basket including two loops is illustrated in FIGS. 13A-13C. This method features pairing two elongated loops 12 together as shown in FIG. 13A. The proximal end 109 of each of the loops 12 is attached to an elongated member 20 through a base cannula 100 illustrated in FIG. 13B, or other means, and the opposite, distal ends 14 of the loops 12 remain free. Alternatively, the proximal ends 109 of the loops 12 can be twisted together to form the elongated member 20, shown in FIG. 13C.

Retrieval baskets having three, four, or more loops can also be formed according to this method and the basket forming method illustrated in FIGS. 13A-13C is not intended to be limited to only the two loop embodiment illustrated.

Figure 15A:
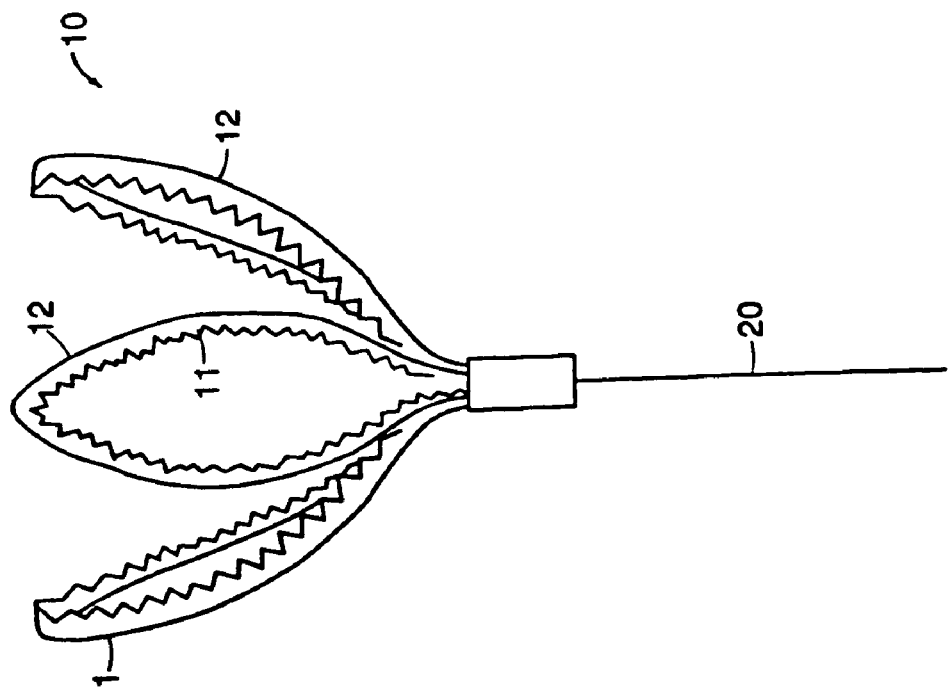
FIG. 15A illustrates an embodiment of a basket according to the invention.
Figure 15B:
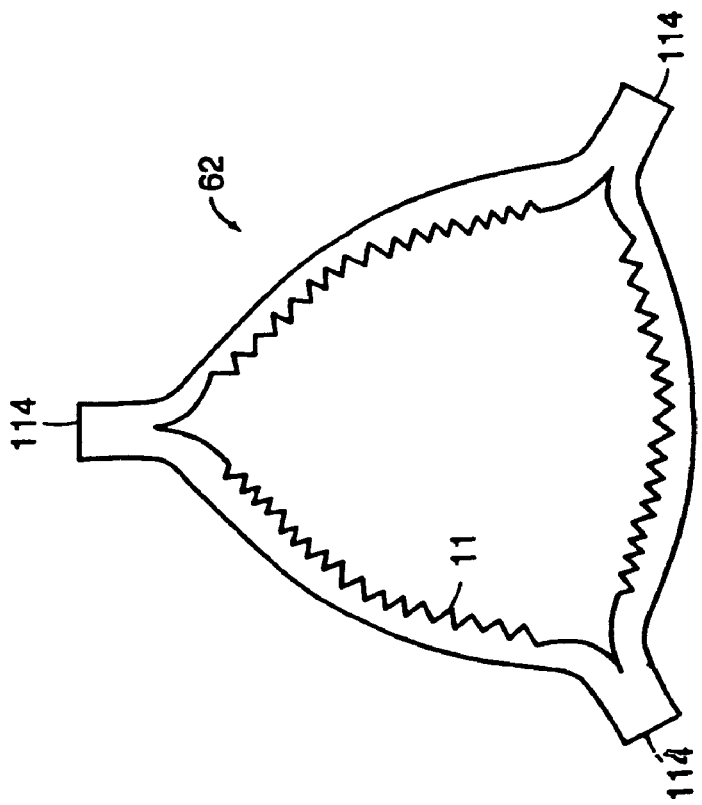
FIG. 15B illustrates an embodiment of a shape for forming the basket illustrated in FIG. 15A according to the invention.

Any of the wire baskets according to the invention, may use one or more wires 116 having any one of a variety of cross-sections. The ends of the wires forming the basket may extend proximally all or part of the way to the handle to form the elongated member. For example, illustrated in FIGS. 14A-14F, the cross-section of the wires 116 may be round, oval, square, rectangular, or D-shaped. A feature of wire 116 including a round cross-section, is a flattened mid-section 118, illustrated in FIG. 14F. The flattened section 118 can form the distal or free end 14 of the loop, and the two end-sections 119 with round cross-sections form the remaining portions of the loop and/or all, or a portion of the elongated member 20 illustrated in FIG. 14G. P The inner edge 11 of any of the basket loops according to the invention may be roughened, for example, by serrations or teeth, as shown in FIG. 9D, and FIGS. 15A, or by etched surfaces, or pointed raised structures. Particles also may be applied to the inner edge 11 to improve gripping of the loops 12 on an object. One or more of the basket loops 12 may have such a rough inner edge 11. The roughened edge may be incorporated into the frame 62 when it is removed from a single piece of material, illustrated in FIGS. 9E and 15B. Alternatively, the roughened edge may be applied after the frame 62 is constructed but before the frame 62 is folded into a three-dimensional basket. The inner edge 11 of the loop members can instead or additionally be treated with an anti-slip material such as a plastic composite or a rubberized coating before the frame 62 is folded into a three dimensional basket frame with loops.

In another aspect of the invention, referring to FIGS. 16A-16C, the medical retrieval device 10 has two sheaths, an outer sheath 18 and an inner sheath 19. The outer sheath has a longitudinally disposed lumen 22, and the inner sheath has a longitudinally disposed lumen 22'. The inner sheath 19 is axially disposed in the lumen of the outer sheath 18. An elongated member 20 is axially disposed in the lumen 22' of the inner sheath 19 and attached at a distal end to the basket base 15. The basket 10 is moveable between an open position, illustrated in FIG. 16B when the basket 10 is extended beyond the distal end of the inner sheath 19 and outer sheath 18, and a closed position, illustrated in FIG. 16A, when the basket 10 is retracted into the lumen 22' of the inner sheath 19. The basket 10 moves between the open and closed position either by axial movement of the elongated member 20 relative to a stationary sheath 19, or by axial movement of the inner sheath 19 over the basket 10 relative to a stationary elongated member 20 as described above.

In a two sheath embodiment, the basket 10, illustrated in FIG. 16A, is advanced in its closed position adjacent a stone 31. The basket 10, illustrated in FIG. 16B, is extended from the distal end of the inner sheath 19 and outer sheath 18, and opened. The stone 31 is captured by the basket 10 and the inner sheath 19 is moved relative to the basket 10 to collapse the basket 10 around the stone 31 thereby grasping the stone 31 more firmly. The basket 10, stone 31, and inner sheath 19 are retracted into the lumen 22 of the outer sheath 18 and the medical retrieval device 8 is removed from the body.

Variations, modifications, and other implementations of what is described herein will occur to those of ordinary skill in the art without departing from the spirit and the scope of the invention as claimed. Accordingly, the invention is to be defined not by the preceding description but instead by the spirit and scope of the following claims.

What is claimed is:

1. A medical retrieval device comprising:
   a proximal handle;
   a sheath extending distally from the handle and including a lumen extending therethrough from a distal end of the sheath to a proximal end of the sheath;
   only two opposing loops comprised of a single piece of unitary material, the loops having a first position in which the loops are collapsed within the lumen of the sheath and a second position in which the loops are extended from the distal end of the sheath and out of the lumen, the loops being joined at a base and unattached to each other at their distal ends, the loops being moveable between an open position and a closed position with the loops being closer together at their distal ends when in the closed position than when in the open position to allow capture and release of material; and
   an elongate member having a first portion, an intermediate portion, and a second portion, the intermediate portion disposed between the first portion and second portion, wherein the intermediate portion is configured to pass through the two opposing loops proximate to the base of the two opposing loops.

2. The medical retrieval device of claim 1, further including a tubular member having a lumen therein, wherein the intermediate portion of the elongate member and the base of the loops are retained within the tubular member.

3. The medical retrieval device of claim 2, wherein a distal portion of the tubular member abuts a proximal portion of the loops.

4. A medical retrieval device comprising:
   first and second opposing loops each having a proximal end and a distal end, wherein the loops are joined at the proximal ends of the loops and are unattached at the distal ends of the loops;
   an elongate member having a first portion, an intermediate portion, and a second portion, the intermediate portion disposed between the first portion and second portion, wherein the intermediate portion is configured to pass through the loops proximate to the proximal ends of the loops; and
   a tubular member having a lumen therein, wherein the intermediate portion of the elongate member and the proximal ends of the loops are fixedly retained within the tubular member;
   wherein the loops are moveable between an open position and a closed position with the loops being closer together at their distal ends when in the closed position than when in the open position to allow capture and release of material.

5. The medical retrieval device of claim 4, wherein the loops are comprised of a single piece of unitary material.

6. The medical retrieval device of claim 4, wherein a distal portion of the tubular member abuts the proximal ends of the loops.

7. The medical retrieval device of claim 6, further including adhesive disposed on the tubular member.

8. The medical retrieval device of claim 4, wherein at least a portion of at least one of the first and second opposing loops includes at least one of serrations, anti-slip material, an energy receiving surface, a cutting surface, teeth, an etched surface, and a pointed raised structure.

9. The medical retrieval device of claim 4, further including support members disposed between the opposing loops, wherein the support members attach to the loops between the proximal end and the distal end of the loops.

10. The medical retrieval device of claim 4, further including one or more additional loops, wherein the one or more additional loops are joined at their proximal ends to the first and second loops and are unattached at their distal ends.

11. The medical retrieval device of claim 4, wherein the loops have an intermediate position, between the open position and closed position, in which the loops are partially opened at their unattached ends.

* * * * *